US007452885B2

(12) United States Patent
Zhou et al.

(10) Patent No.: US 7,452,885 B2
(45) Date of Patent: Nov. 18, 2008

(54) AMINO-5-(6-MEMBERED)HETEROARYLIMIDAZOLONE COMPOUNDS AND THE USE THEREOF FOR β-SECRETASE MODULATION

(75) Inventors: Ping Zhou, Plainsboro, NJ (US); Michael Sotirios Malamas, Jamison, PA (US); Yanfang Li, Lawrenceville, NJ (US); Albert Jean Robichaud, Ringoes, NJ (US); Dominick Anthony Quagliato, Bridgewater, NJ (US)

(73) Assignee: Wyeth, Madison, NJ (US)

( * ) Notice: Subject to any disclaimer, the term of this patent is extended or adjusted under 35 U.S.C. 154(b) by 174 days.

(21) Appl. No.: 11/478,098

(22) Filed: Jun. 29, 2006

(65) Prior Publication Data
US 2007/0004730 A1    Jan. 4, 2007

Related U.S. Application Data

(60) Provisional application No. 60/695,305, filed on Jun. 30, 2005.

(51) Int. Cl.
*C07D 403/04* (2006.01)
*A61K 31/4439* (2006.01)

(52) U.S. Cl. .................. 514/252.05; 514/256; 514/340; 514/341; 544/238; 544/333; 546/268.4; 546/272.7

(58) Field of Classification Search ............... 546/272.7
See application file for complete search history.

(56) References Cited

U.S. PATENT DOCUMENTS

| 4,140,793 | A | 2/1979 | Ward |
| 4,225,613 | A | 9/1980 | Ward |
| 6,054,457 | A | 4/2000 | Setoi et al. |
| 6,399,824 | B1 | 6/2002 | Hofmeister et al. |
| 6,656,957 | B1 | 12/2003 | Allgeier et al. |
| 6,689,804 | B2 | 2/2004 | Wu et al. |
| 6,974,829 | B2 | 12/2005 | Tung et al. |
| 7,285,682 | B2 | 10/2007 | Hu |
| 2005/0282825 | A1 | 12/2005 | Malamas et al. |
| 2005/0282826 | A1 | 12/2005 | Malamas et al. |
| 2006/0111370 | A1 | 5/2006 | Zhu et al. |
| 2006/0160828 | A1 | 7/2006 | Malamas et al. |
| 2006/0173049 | A1 | 8/2006 | Malamas et al. |
| 2006/0182792 | A1 | 8/2006 | Fobare et al. |
| 2006/0183790 | A1 | 8/2006 | Cole et al. |
| 2007/0004786 | A1 | 1/2007 | Malamas et al. |
| 2007/0027199 | A1 | 2/2007 | Malamas et al. |
| 2007/0072925 | A1 | 3/2007 | Malamas et al. |
| 2007/0191431 | A1 | 8/2007 | Zhou |
| 2007/0203116 | A1 | 8/2007 | Quagliato et al. |
| 2008/0051390 | A1 | 2/2008 | Malamas et al. |

FOREIGN PATENT DOCUMENTS

| EP | 0861831 A1 | 9/1998 |
| GB | 2013192 A | 8/1979 |
| WO | WO 07/45417 A1 | 12/1997 |
| WO | WO 98/45267 | 10/1998 |
| WO | WO 01/87829 A1 | 11/2001 |
| WO | WO 03/053938 A1 | 7/2003 |
| WO | WO 03/064396 A1 | 8/2003 |
| WO | WO 03/094854 A2 | 11/2003 |
| WO | WO 2004/058757 A1 | 7/2004 |
| WO | WO 2005/005412 A1 | 1/2005 |
| WO | WO 2005/058311 A1 | 6/2005 |
| WO | WO 2006/009653 A1 | 1/2006 |
| WO | WO 2006/065277 A2 | 6/2006 |
| WO | WO 2007/005404 A1 | 1/2007 |
| WO | WO 2007/016012 A2 | 2/2007 |

OTHER PUBLICATIONS

Heras et al, Tetrahedron, 2001, vol. 57, pp. 4371-4388.*
PCT Prelimnary Report on Patentability, Written Opinion of the ISR, corresponding PCT international application PCT/US2006/024912, international filing date Jun. 26, 2006.
Abbott et al., Molecular Medicine Today, 1996, vol. 2, p. 106-113.
Allimony et al., "Synthesis and antimicrobial activity of some nitrogen heterobicyclic systems: Part I", Indian Journal of Chemistry, 1999, vol. 38B, pp. 445-451.
Fact Sheet Alzheimer's Association, 2006.
Lefrance-Jullien et al., "Design and characterization of a new cell-permeant inhibitor of the beta-secretase BACE1", British Journal of Pharmacology, 2005, vol. 145, pp. 228-235.
Lyketsos et al., "Position statement of the American Association for Geriatric Psychiatry regarding principles of care for patients with dementia resulting from Alzheimer's Disease", 2006, vol. 14, pp. 561-573.

(Continued)

*Primary Examiner*—Zinna N Davis
(74) *Attorney, Agent, or Firm*—Andrea Dorigo; Scott K. Larsen

(57) ABSTRACT

The present invention provides a 2-amino-5-heteroaryl-5-phenylimidazolone compound of formula I

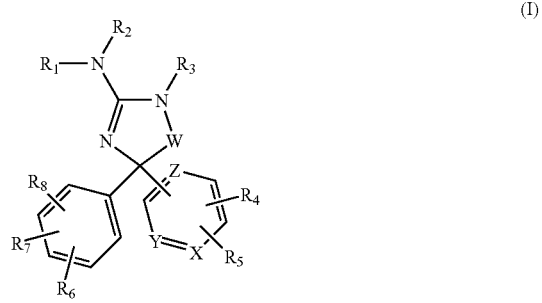

(I)

The present invention also provides methods for the use thereof to inhibit β-secretase (BACE) and treat β-amyloid deposits and neurofibrillary tangles.

15 Claims, No Drawings

OTHER PUBLICATIONS

Alzheimer's Disease, retrieved from internet on Jun. 27, 2007, http://www.mayoclinic.com/health/alzheimers-disease/DA00161/DSECTION-3.

National Institute of Neurological Discorders and Stroke, "Alzheimer's Disease Information Page", retrieved from internet on Jun. 27, 2007, http://www.ninds.nih.gov/disorders/alzheimersdisease/alzheimersdisease.htm.

PCT Preliminary Report on Patentability, Written Opinion of the ISR, International Patent Application PCT/US2006/024793, International filing date Jun. 26, 2006.

Selkoe, "Alzheimer's Disease: Genes, Proteins, and Therapy", Physiological Reviews, 2001, vol. 81(2), pp. 741-766.

Su et al., "Drug delivery across the blood-brain barrier: why is it difficult? How to measure and improve it?", Expert Opinion on Drug Delivery, Abstract, 2006, vol. 3, pp. 419-425.

Tao et al., "Synthesis of Conformationally constrained spirohydantoins with a Dibenzo[a,d]heptadiene ring", Synthesis 2000, No. 10, pp. 1449-1453.

Vandana et al., "Transferring coupled liposomes as drug delivery carriers for brain trageting of 5-florouracil", Journal of Drug Targeting, Abstract, 2005, vol. 13 pp. 245-250.

Varghese et al., "Human beta-secretase (BACE) and BACE Inhibitors", J. Med. Chem. 2003, vol. 46(22), pp. 4625-4630.

Xiao et al., "An improved procedure for the synthesis of 4,4-disubstituted-3-oxo-1,2,5-thiadiazolidine 1,1-dioxides", J. Heterocyclic Chem., 2000, vol. 37, pp. 773-777.

Yamada et al., "Hydantoin derivaties, I. Actions on central nervous system of 5,5-diarylhydantoins and 5,5-diarylhydantion-2-imines", Abstract, Oyo Yakuri, 1975, vol. 9(6), pp. 841-847.

* cited by examiner

AMINO-5-(6-MEMBERED)HETERO ARYLIMIDAZOLONE COMPOUNDS AND THE USE THEREOF FOR β-SECRETASE MODULATION

This application claims the benefit under 35 U.S.C. §119 (e) to U.S. Provisional Application No. 60/695,305, filed Jun. 30, 2005, which is hereby incorporated by reference in its entirety.

BACKGROUND OF THE INVENTION

β-Amyloid deposits and neurofibrillary tangles are two major pathologic characterizations associated with Alzheimer's disease (AD). Clinically, AD is characterized by the of loss of memory, cognition, reasoning, judgment, and orientation. Also affected, as the disease progresses, are motor, sensory, and linguistic abilities until global impairment of multiple cognitive functions occurs. These cognitive losses take place gradually, but typically lead to severe impairment and eventual death in 4-12 years.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders disorders (Varghese, J., et al, Journal of Medicinal Chemistry, 2003, 46, 4625-4630).

β-amyloid deposits are predominately an aggregate of Aβ peptide, which in turn is a product of the proteolysis of amyloid precursor protein (APP). More specifically, Aβ peptide results from the cleavage of APP at the C-terminus by one or more γ-secretases, and at the N-terminus by β-secretase enzyme (BACE), also known as aspartyl protease, as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide (Roberds, S. L., et al, Human Molecular Genetics, 2001, 10, 1317-1324).

Therefore, it is an object of this invention to provide compounds which are inhibitors of β-secretase and are useful as therapeutic agents in the treatment, prevention or amelioration of a disease or disorder characterized by elevated β-amyloid deposits or β-amyloid levels in a patient.

It is another object of this invention to provide therapeutic methods and pharmaceutical compositions useful for the treatment, prevention or amelioration of a disease or disorder characterized by elevated β-amyloid deposits or β-amyloid levels in a patient.

It is a feature of this invention that the compounds provided may also be useful to further study and elucidate the β-secretase enzyme.

These and other objects and features of the invention will become more apparent by the detailed description set forth hereinbelow.

SUMMARY OF THE INVENTION

The present invention provides a compound of formula I

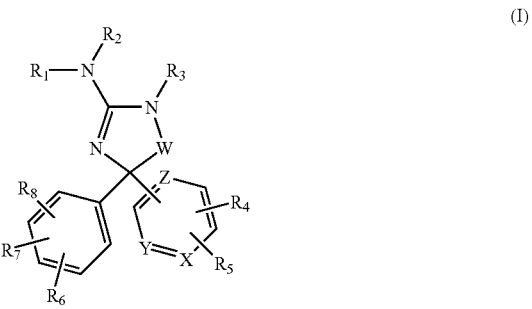

wherein
W is CO, CS or $CH_2$;
X is N, NO, or CR;
Y is N, NO, or $CR_{10}$;
Z is N, NO, or $CR_{11}$ with the proviso that at least one of X, Y or Z must be N or NO;
$R_1$ and $R_2$ are each independently H, $COR_{34}$, $CO_2R_{12}$ or an optionally substituted $C_1$-$C_4$alkyl group;
$R_3$ is H, $OR_{13}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl($C_1$-$C_6$)alkyl group each optionally substituted;
$R_4$ and $R_5$ are each independently H, halogen, $NO_2$, CN, $OR_{14}$, $CO_2R_{15}$, $COR_{16}$, $NR_{17}R_{18}$, $SO_pNR_{19}R_{20}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
$R_6$ is H, halogen, $NO_2$, CN, $OR_{21}$, $NR_{22}R_{23}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
$R_7$ is H, halogen, $NO_2$, CN, $OR_{24}$, $NR_{25}R_{26}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, aryl or heteroaryl group each optionally substituted;
R, $R_8$, $R_9$ and $R_{10}$ are each independently H, halogen, $NO_2$, CN, $OR_{27}$, $CO_2R_{28}$, $COR_{29}$, $NR_3OR_{31}$, $SO_pNR_{32}R_{33}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
$R_{11}$, $R_{12}$, $R_{13}$, $R_{14}$, $R_{15}$, $R_{16}$, $R_{21}$, $R_{24}$, $R_{27}$, $R_{28}$ and $R_{29}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl or aryl group each optionally substituted;
$R_{17}$, $R_{18}$, $R_{19}$, $R_{20}$, $R_{22}$, $R_{23}$, $R_{25}$, $R_{26}$, $R_{30}$, $R_{31}$, $R_{32}$ and $R_{33}$ are each independently H, $COR_{34}$, $SO_pR_{35}$ or a $C_1$-$C_4$alkyl, $C_2$-$C_6$alkenyl, $C_2$-$C_6$alkynyl, $C_3$-$C_8$cycloalkyl, cycloheteroalkyl, aryl or heteroaryl group each optionally substituted or $R_{17}$, $R_{18}$; or $R_{19}$, $R_{20}$, or $R_{22}$, $R_{23}$, or $R_{25}$, $R_{26}$, or $R_{30}$, $R_{31}$, or $R_{32}$, $R_{33}$ may be taken together with the atom to which they are attached to form an optionally substituted 5- to 7-membered ring optionally containing an additional heteroatom selected from O, N or S;
$R_{34}$ is H, or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted; and $R_{35}$ is a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted; or a tautomer thereof, a stereoisomer thereof or a pharmaceutically acceptable salt thereof.

The present invention also relates to the use of the formula I heteroarylimidazolone compound for the treatment of β-amyloid deposits and neurofibrillary tangles. The compound of the invention is particularly useful for treating Alzheimer's disease, cognitive impairment, Down's Syndrome, HCHWA-D, cognitive decline, senile dementia, cerebral amyloid angiopathy, degenerative dementia, or other neurodegenerative disorders.

DETAILED DESCRIPTION OF THE INVENTION

Alzheimer's disease (AD) is a major degenerative disease of the brain which presents clinically by progressive loss of memory, cognition, reasoning, judgement and emotional stability and gradually leads to profound mental deteoriation and death. The exact cause of AD is unknown, but increasing evidence indicates that amyloid beta peptide (A-beta) plays a central role in the pathogenesis of the disease. (D. B. Schenk; R. E. Rydel et al, Journal of Medicinal Chemistry, 1995, 21, 4141 and D. J. Selkoe, Physiology Review, 2001, 81, 741). Patients with AD exhibit characteristic neuropathological markers such as neuritic plaques (and in β-amyloid angiopathy, deposits in cerebral blood vessels) as well as neurofibrillary tangles detected in the brain at autopsy. A-beta is a major component of neuritic plaques in AD brains. In addition, β-amyloid deposits and vascular β-amyloid angiopathy also characterize individuals with Downs Syndrome, Hereditary Cerebral Hemmorhage with Amyloidosis of the Dutch type and other neurodegenreative and dementia-inducing disorders. Over expression of the amyloid precursor protein (APP), altered cleavage of APP to A-beta or a decrease in the clearance of A-beta from a patient's brain may increase the levels of soluble or fibrullar forms of A-beta in the brain. The β-site APP cleaving enzyme, BACE1, also called memapsin-2 or Asp-2, was identified in 1999 (R. Vassar, B. D. Bennett, et al., Nature, 1999, 402, 537). BACE1 is a membrane-bound aspartic protease with all the known functional properties and characteristics of β-secretase. Low molecular weight, non-peptide, non-substrate-related inhibitors of BACE1 or β-secretase are earnestly sought both as an aid in the study of the β-secretase enzyme and as potential therapeutic agents.

Surprisingly, it has now been found that amino-5-heteroarlyimidazolone compounds of formula I demonstrate inhibition of β-secretase and the selective inhibition of BACE1. Advantageously, said heteroarlyimidazolone compounds may be used as effective therapeutic agents for the treatment, prevention or amelioration of a disease or disorder characterized by elevated β-amyloid deposits or β-amyloid levels in a patient. Accordingly, the present invention provides an amino-5-heteroarylimidazolone compound of formula I

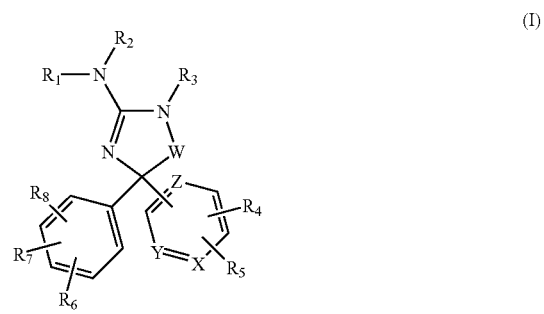

wherein

W is CO, CS or $CH_2$;

X is N, NO, or CR;

Y is N, NO, or $CR_{10}$;

Z is N, NO, or $CR_{11}$ with the proviso that at least one of X, Y or Z must be N or NO;

$R_1$ and $R_2$ are each independently H, $COR_{34}$, $CO_2R_{12}$ or an optionally substituted $C_1$-$C_4$alkyl group;

$R_3$ is H, $OR_{13}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl ($C_1$-$C_6$)alkyl group each optionally substituted;

$R_4$ and $R_5$ are each independently H, halogen, $NO_2$, CN, $OR_{14}$, $CO_2R_{15}$, $COR_{16}$, $NR_{17}R_{18}$, $SO_pNR_{19}R_{20}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;

$R_6$ is H, halogen, $NO_2$, CN, $OR_{21}$, $NR_{22}R_{23}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;

$R_7$ is H, halogen, $NO_2$, CN, $OR_{24}$, $NR_{25}R_{26}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, aryl or heteroaryl group each optionally substituted;

R, $R_8$, $R_9$ and $R_{10}$ are each independently H, halogen, $NO_2$, CN, $OR_{27}$, $CO_2R_{28}$, $COR_{29}$, $NR_3OR_{31}$, $SO_pNR_{32}R_{33}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;

$R_{11}$, $R_{12}$, $R_{13}$, $R_{14}$, $R_{15}$, $R_{16}$, $R_{21}$, $R_{24}$, $R_{27}$, $R_{28}$ and $R_{29}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl or aryl group each optionally substituted;

$R_{17}$, $R_{18}$, $R_{19}$, $R_{20}$, $R_{22}$, $R_{23}$, $R_{25}$, $R_{26}$, $R_{30}$, $R_{31}$, $R_{32}$ and $R_{33}$ are each independently H, $COR_{34}$, $SO_pR_{35}$ or a $C_1$-$C_4$alkyl, $C_2$-$C_6$alkenyl, $C_2$-$C_6$alkynyl, $C_3$-$C_8$ cycloalkyl, cycloheteroalkyl, aryl or heteroaryl group each optionally substituted or $R_{17}$, $R_{18}$; or $R_{19}$, $R_{20}$, or $R_{22}$, $R_{23}$, or $R_{25}$, $R_{26}$, or $R_{30}$, $R_{31}$, or $R_{32}$, $R_{33}$ may be taken together with the atom to which they are attached to form an optionally substituted 5- to 7-membered ring optionally containing an additional heteroatom selected from O, N or S;

R$_{34}$ is H, or a C$_1$-C$_6$alkyl, C$_1$-C$_6$haloalkyl, C$_2$-C$_6$alkenyl, C$_2$-C$_6$alkynyl, C$_3$-C$_8$cycloalkyl, cycloheteroalkyl, aryl or heteroaryl group each optionally substituted; and R$_{35}$ is a C$_1$-C$_6$alkyl, C$_1$-C$_6$haloalkyl, C$_2$-C$_6$alkenyl, C$_2$-C$_6$alkynyl, C$_3$-C$_8$cycloalkyl, cycloheteroalkyl, aryl or heteroaryl group each optionally substituted; or a tautomer thereof, a stereoisomer thereof or a pharmaceutically acceptable salt thereof.

It is understood that the claims encompass all possible stereoisomers and prodrugs. Moreover, unless stated otherwise, each alkyl, alkenyl, alkynyl, cycloalkyl cycloheteroalkyl, aryl or heteroaryl group is contemplated as being optionally substituted.

An optionally substituted moiety may be substituted with one or more substituents. The substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Unless otherwise specified, typically, 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms.

As used herein, the term "alkyl" includes both (C$_1$-C$_{10}$) straight chain and (C$_3$-C$_{12}$) branched-chain (unless defined otherwise) monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like. Specifically included within the definition of "alkyl" are those alkyl groups that are optionally substituted. Suitable alkyl substitutions include, but are not limited to, CN, OH, halogen, phenyl, carbamoyl, carbonyl, alkoxy or aryloxy.

As used herein the term "haloalkyl" designates a C$_n$H$_{2n+1}$ group having from one to 2n+1 halogen atoms which may be the same or different. Examples of haloalkyl groups include CF$_3$, CH$_2$Cl, C$_2$H$_3$BrCl, C$_3$H$_5$F$_2$, or the like.

The term "alkenyl", as used herein, refers to either a (C$_2$-C$_8$) straight chain or (C$_3$-C$_{10}$) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, or the like.

The term "cycloalkyl", as used herein, refers to a monocyclic, bicyclic, tricyclic, fused, bridged, or spiro monovalent saturated hydrocarbon moiety of 3-10 carbon atoms, unless otherwise specified, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, or the like.

The term "cycloheteroalkyl" as used herein designates a C$_5$-C$_7$cycloalkyl ring system containing 1, 2 or 3 heteroatoms, which may be the same or different, selected from N, O or S and optionally containing one double bond. Exemplary of the cycloheteroalkyl ring systems included in the term as designated herein are the following rings wherein X$_1$ is NR', O or S and R is H or an optional substituent as defined hereinbelow.

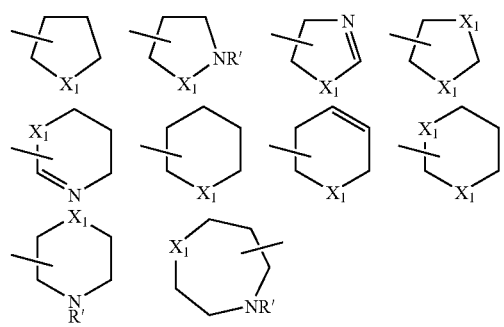

The term "aryl", as used herein, refers to an aromatic carbocyclic moiety of up to 20 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. The term "aryl" further includes both unsubstituted carbocylic groups and carbocylic groups containing 1-5-substitutions.

The term "heteroaryl" as used herein means an aromatic heterocyclic ring system, which may be a single ring (monocyclic) or multiple rings (bicyclic, up to three rings) fused together or linked covalently. Preferably, heteroaryl is a 5- to 6-membered ring. The rings may contain from one to four hetero atoms selected from nitrogen, oxygen, or sulfur, wherein the nitrogen or sulfur atom(s) are optionally oxidized, or the nitrogen atom(s) are optionally quarternized. Any suitable ring position of the heteroaryl moiety may be covalently linked to the defined chemical structure. Examples of heteroaryl moieties include, but are not limited to, heterocycles such as furan, thiophene, pyrrole, N-methylpyrrole, pyrazole, N-methylpyrazole, imidazole, N-methylimidazole, oxazole, isoxazole, thiazole, isothiazole, 1H-tetrazole, 1-methyltetrazole, 1,3,4-oxadiazole, 1H-1,2,4-triazole, 1-methyl-1,2,4-triazole 1,3,4-triazole, 1-methyl-1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, α-carboline, or the like.

The term "halogen", as used herein, designates fluorine, chlorine, bromine, and iodine.

The compounds of the present invention may be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethyl-propylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included. The term "pharmaceutically acceptable salt", as used herein, refers to salts derived form organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Compounds of the invention may exist as one or more tautomers. One skilled in the art will recognize that compounds of formula I may also exist as the tautomer It as shown below.

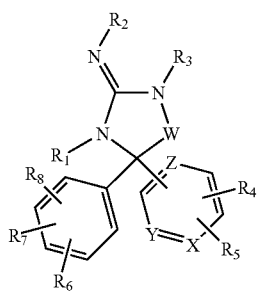

(It)

Tautomers often exist in equilibrium with each other. As these tautomers interconvert under environmental and physiological conditions, they provide the same useful biological effects. The present invention includes mixtures of such tautomers as well as the individual tautomers of Formula I and Formula It.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one steriosomer, preferably less than about 50%, more preferably less than about 75%, and even more preferably less than about 90%.

Preferred compounds of formula I are those compounds wherein W is CO; X is N; Y is $CR_{10}$ and Z is $CR_{11}$. Another group of preferred compouonds is those compounds of formula I wherein W is CO and $R_7$ is phenyl or heteroaryl. Also preferred are those compounds of formula I wherein W is CO; $R_1$ and $R_2$ are H; and $R_3$ is H or $C_1$-$C_3$alkyl.

More preferred compounds of the invention are those compounds of formula I wherein W is CO; X is N; Y is $CR_{10}$; Z is $CR_{11}$; and $R_7$ is phenyl or heteroaryl. Another group of more preferred compounds of the invention are those compounds of formula I wherein W is CO; X is N; Y is $CR_{10}$; Z is $CR_{11}$; $R_7$ is phenyl or heteroaryl; and $R_1$ and $R_2$ are H A further group of more preferred compounds of the invention are those compounds of formula I wherein W is CO; X is N; Y is $CR_{10}$; Z is $CR_{11}$; $R_7$ is phenyl or heteroaryl; $R_1$ and $R_2$ are H; and $R_3$ is methyl.

Preferred compounds of the invention include:
(5S)-2-amino-5-[4-fluoro-3-(2-fluoropyridin-3-yl)phenyl]-3-methyl-5-pyridin-4-yl-3,5-dihydro-4H-imidazol-4-one;
2-amino-3-methyl-5-phenyl-5-pyridin-4-yl-3,5-dihydro-4H-imidazol-4-one;
2-amino-5-(3-bromophenyl)-3-methyl-5-pyridin-4-yl-3,5-dihydro-4H-imidazol-4-one;
2-amino-5-(3-methoxyphenyl)-3-methyl-5-pyridin-4-yl-3,5-dihydro-4H-imidazol-4-one;
2-amino-5-(1,1'-biphenyl-3-yl)-3-methyl-5-pyridin-4-yl-3,5-dihydro-4H-imidazol-4-one;
2-amino-5-(1,1'-biphenyl-3-yl)-3-methyl-5-pyridin-3-yl-3,5-dihydro-4H-imidazol-4-one;
2-amino-3-methyl-5-phenyl-5-pyridin-3-yl-3,5-dihydro-4H-imidazol-4-one;
2-amino-5-(3-hydroxyphenyl)-3-methyl-5-pyridin-4-yl-3,5-dihydro-4H-imidazol-4-one;
2-amino-5-(3'-fluoro-1,1'-biphenyl-3-yl)-3-methyl-5-pyridin-4-yl-3,5-dihydro-4H-imidazol-4-one;
2-amino-5-(3',5'-difluoro-1,1'-biphenyl-3-yl)-3-methyl-5-pyridin-4-yl-3,5-dihydro-4H-imidazol-4-one;
2-amino-5-(2',5'-difluoro-1,1'-biphenyl-3-yl)-3-methyl-5-pyridin-4-yl-3,5-dihydro-4H-imidazol-4-one;
2-amino-3-methyl-5-pyridin-4-yl-5-[3'-(trifluoromethyl)-1,1'-biphenyl-3-yl]-3,5-dihydro-4H-imidazol-4-one;
2-amino-3-methyl-5-pyridin-4-yl-5-[3'-(trifluoromethoxy)-1,1'-biphenyl-3-yl]-3,5-dihydro-4H-imidazol-4-one;
3'-(2-amino-1-methyl-5-oxo-4-pyridin-4-yl-4,5-dihydro-1H-imidazol-4-yl)-1,1'-biphenyl-3-carbonitrile;
2-amino-3-methyl-5-(3-pyrazin-2-ylphenyl)-5-pyridin-4-yl-3,5-dihydro-4H-imidazol-4-one;
2-amino-5-(3'-methoxy-1,1'-biphenyl-3-yl)-3-methyl-5-pyridin-4-yl-3,5-dihydro-4H-imidazol-4-one;
2-amino-5-(3'-hydroxy-1,1'-biphenyl-3-yl)-3-methyl-5-pyridin-4-yl-3,5-dihydro-4H-imidazol-4-one;
2-amino-5-(1,1'-biphenyl-3-yl)-3-methyl-5-(2-methylpyridin-4-yl)-3,5-dihydro-4H-imidazol-4-one;
2-amino-5-(2',5'-difluoro-1,1'-biphenyl-3-yl)-3-methyl-5-(2-methylpyridin-4-yl)-3,5-dihydro-4H-imidazol-4-one;
2-amino-5-(2',5'-difluoro-1,1'-biphenyl-3-yl)-5-(2-ethylpyridin-4-yl)-3-methyl-3,5-dihydro-4H-imidazol-4-one;
2-amino-5-(2',5'-difluoro-1,1'-biphenyl-3-yl)-3-methyl-5-(2-propylpyridin-4-yl)-3,5-dihydro-4H-imidazol-4-one;
2-amino-5-(2',5'-difluoro-1,1'-biphenyl-3-yl)-5-(2-isopropylpyridin-4-yl)-3-methyl-3,5-dihydro-4H-imidazol-4-one;

2-amino-5-(2',5'-difluoro-1,1'-biphenyl-3-yl)-5-(2-fluoropyridin-4-yl)-3-methyl-3,5-dihydro-4H-imidazol-4-one;
2-amino-5-(2',5'-difluoro-1,1'-biphenyl-3-yl)-5-(3-fluoropyridin-4-yl)-3-methyl-3,5-dihydro-4H-imidazol-4-one;
2-amino-3-methyl-5-pyridin-4-yl-5-(3-thien-2-ylphenyl)-3,5-dihydro-4H-imidazol-4-one;
2-amino-3-methyl-5-pyridin-4-yl-5-(3-thien-3-ylphenyl)-3,5-dihydro-4H-imidazol-4-one;
2-amino-5-[3-(2-furyl)phenyl]-3-methyl-5-pyridin-4-yl-3,5-dihydro-4H-imidazol-4-one;
2-amino-5-[3-(3-furyl)phenyl]-3-methyl-5-pyridin-4-yl-3,5-dihydro-4H-imidazol-4-one;
2-amino-3-methyl-5-(3-propoxyphenyl)-5-pyridin-4-yl-3,5-dihydro-4H-imidazol-4-one;
2-amino-5-(3-isobutoxyphenyl)-3-methyl-5-pyridin-4-yl-3,5-dihydro-4H-imidazol-4-one;
2-amino-5-[3-(but-3-ynyloxy)phenyl]-3-methyl-5-pyridin-4-yl-3,5-dihydro-4H-imidazol-4-one;
N-[3-(2-amino-1-methyl-5-oxo-4-pyridin-4-yl-4,5-dihydro-1H-imidazol-4-yl)phenyl]-2-methoxyacetamide;
N-[3-(2-amino-1-methyl-5-oxo-4-pyridin-4-yl-4,5-dihydro-1H-imidazol-4-yl)phenyl]-2-furamide;
3-(2-amino-1-methyl-5-oxo-4-pyridin-4-yl-4,5-dihydro-1H-imidazol-4-yl)-N-propylbenzamide;
2-amino-5-(3-bromophenyl)-3-methyl-5-(2-methylpyridin-4-yl)-3,5-dihydro-4H-imidazol-4-one;
2-amino-3-methyl-5-(2-methylpyridin-4-yl)-5-(3-pyridin-3-ylphenyl)-3,5-dihydro-4H-imidazol-4-one;
2-amino-3-methyl-5-(2-methylpyridin-4-yl)-5-(3-pyrimidin-5-ylphenyl)-3,5-dihydro-4H-imidazol-4-one;
2-amino-5-(2',5'-difluoro-1,1'-biphenyl-3-yl)-3-methyl-5-(2-methylpyridin-4-yl)-3,5-dihydro-4H-imidazol-4-one;
2-amino-5-(2-ethylpyridin-4-yl)-3-methyl-5-(3-pyridin-3-ylphenyl)-3,5-dihydro-4H-imidazol-4-one;
2-amino-5-(2-ethylpyridin-4-yl)-3-methyl-5-(3-pyrimidin-5-ylphenyl)-3,5-dihydro-4H-imidazol-4-one;
2-amino-5-(2',5'-difluoro-1,1'-biphenyl-3-yl)-5-(2-ethylpyridin-4-yl)-3-methyl-3,5-dihydro-4H-imidazol-4-one;
2-amino-3-methyl-5-(2-methylpyridin-4-yl)-5-(3-pyrazin-2-ylphenyl)-3,5-dihydro-4H-imidazol-4-one;
2-amino-5-(2-ethylpyridin-4-yl)-3-methyl-5-(3-pyrazin-2-ylphenyl)-3,5-dihydro-4H-imidazol-4-one;
2-amino-5-(2,6-dimethylpyridin-4-yl)-3-methyl-5-(3-pyridin-3-ylphenyl)-3,5-dihydro-4H-imidazol-4-one;
2-amino-5-(2,6-dimethylpyridin-4-yl)-3-methyl-5-(3-pyrimidin-5-ylphenyl)-3,5-dihydro-4H-imidazol-4-one;
2-amino-5-(2',5'-difluoro-1,1'-biphenyl-3-yl)-5-(2,6-dimethylpyridin-4-yl)-3-methyl-3,5-dihydro-4H-imidazol-4-one;
2-amino-5-(2,6-dimethylpyridin-4-yl)-3-methyl-5-(3-pyrazin-2-ylphenyl)-3,5-dihydro-4H-imidazol-4-one;
2-amino-5-(2,6-diethylpyridin-4-yl)-3-methyl-5-(3-pyridin-3-ylphenyl)-3,5-dihydro-4H-imidazol-4-one;
2-amino-3-methyl-5-pyridin-4-yl-5-(3-pyridin-3-ylphenyl)-3,5-dihydro-4H-imidazol-4-one;

or a tautomer thereof, a stereoisomer thereof or a pharmaceutically acceptable salt thereof.

Compounds of the invention may be prepared employing conventional methods that utilize readily available reagents and starting materials. The reagents used in the preparation of the compounds of this invention can be either commercially obtained or can be prepared by standard procedures described in the literature. Representative compounds of the present invention can be prepared using the following synthetic schemes. The skilled practitioner will know how to make use of variants of these reaction sequences, which in themselves are well known in the art. For example, compounds of formula I wherein W is CO (Ia) may be prepared by reacting a diketone of formula II with an aminoguanidine derivative of formula III in the presence of a base such as a metal carbonate to give the desired formula Ia compound. The reaction is shown in flow diagram I.

FLOW DIAGRAM I

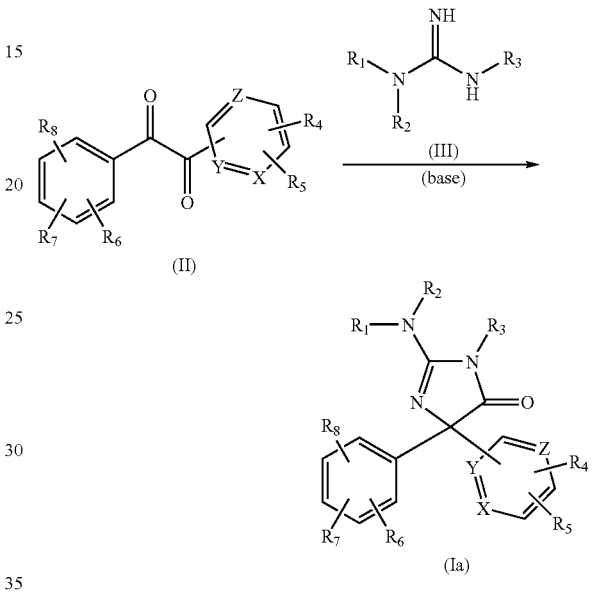

Diketone compounds of formula II may be prepared by reacting an alkyne of formula IV with an oxidizing agent such as Pd(II)Cl/DMSO, N-bromosuccinimide/DMSO, ozone, sodium periodate with ruthenium (IV) oxide hydrate, sulfur trioxide, $KMnO_4$, $I_2$/DMSO, or combinations thereof, preferable $KMnO_4$ and $I_2$/DMSO. The reaction is shown in flow diagram II.

FLOW DIAGRAM II

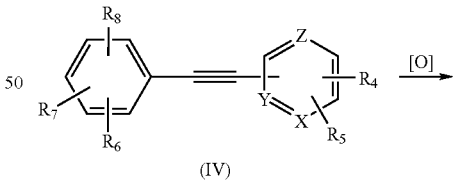

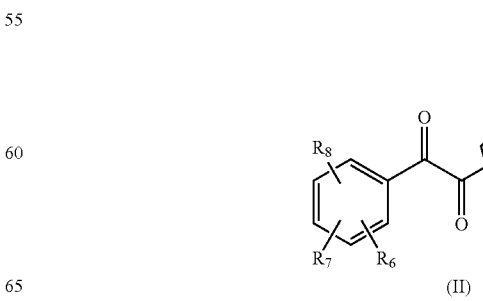

Alkyne compounds of formula IV may be prepared by reacting an aryl compound of formula V wherein L is a leaving group such as Br, I or trifluoromethanesulfonate with a protected acetylene compound of formula VI wherein P is a protecting group such as triaryl(alkyl)silyl or hydroydialkyl(aryl)silyl to give the protected arylalkyne of formula VII; deprotecting the formula VII compound to give the compound of formula VIII using a deprotecting reagent such as a metal or ammonium fluoride, a metal carbonate, for example cesium carbonate or potassium carbonate or a metal hydroxide; and reacting the formula VIII alkyne with a heteroaryl compound of formula IX wherein L represents a leaving group as described hereinabove to give the desired alkyne compound of formula IV. Similarly, compounds of formula IV may be prepared by reversing the order of the coupling the aryl and heteroaryl groups. The reactions are shown in flow diagram III.

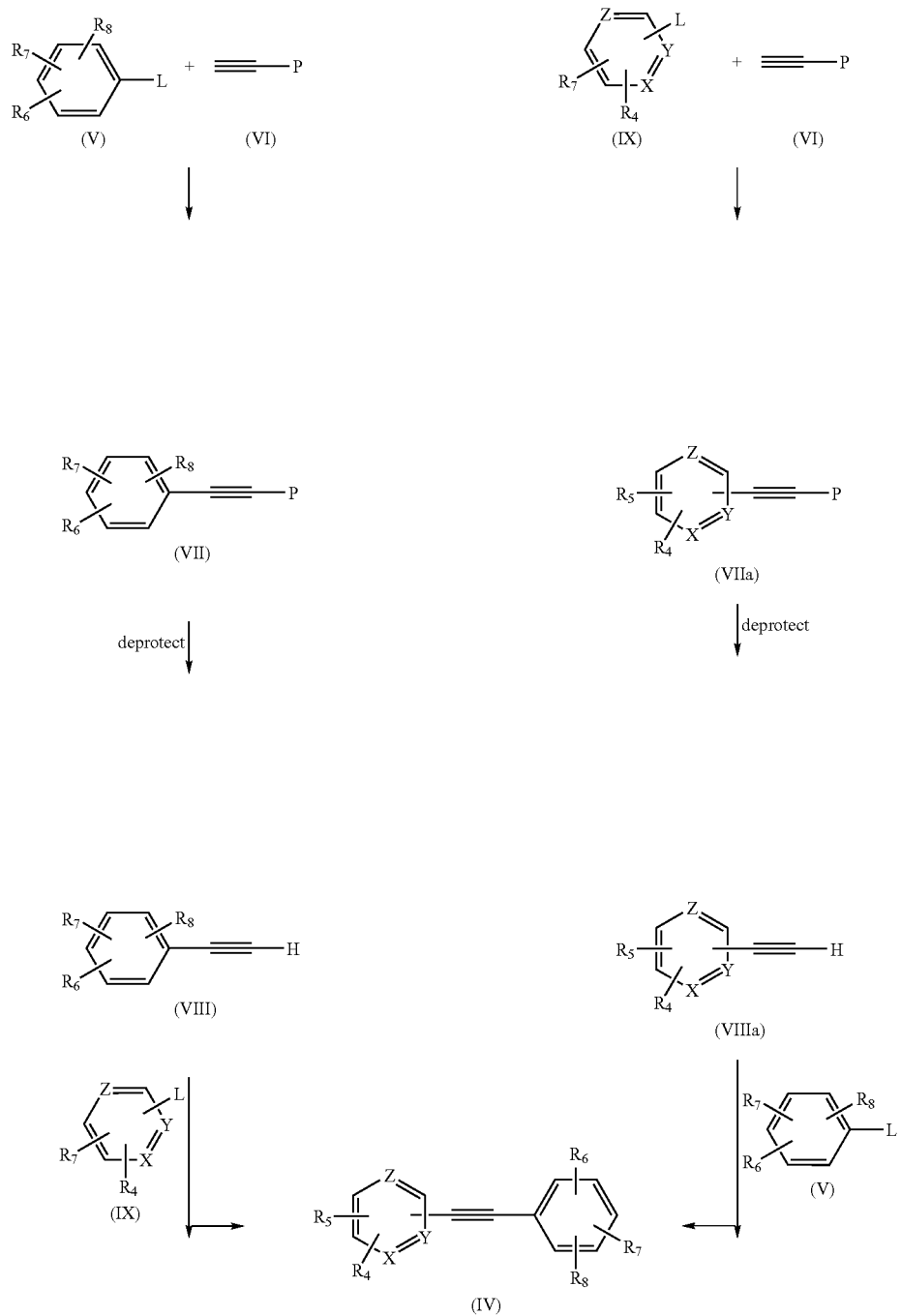

FLOW DIAGRAM III

Alternatively, compounds of formula I wherein $R_7$ is aryl or heteroaryl (Ib) may be prepared following the formation of the hydantoin ring by coupling the appropriate hydantoin compound of formula X with an aryl or heteroaryl boronic acid of formula XI to give the desired compounds of formula Ib. The reaction is shown in flow diagram IV wherein L represents a leaving group as described hereinabove.

FLOW DIAGRAM IV

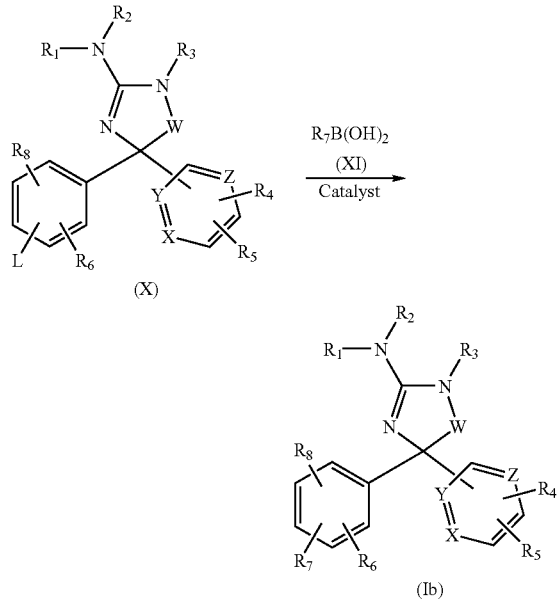

Compounds of formula I wherein W is CS (Ic) may be readily prepared using conventional procedures, such as reacting a compound of formula Ia with $CS_2$ in the presence of a solvent to obtain the desired compound of formula Ic. Similarly, compounds of formula I wherein W is $CH_2$ (Id) may be prepared by reacting a compound of formula Ia with a suitable reducing agent such as $SnCl_2$ to obtain the desired compound of formula Id. The reactions are shown in flow diagram V.

modulating BACE and treating, preventing, or ameliorating β-amyloid deposits and neurofibrillary tangles associated with diseases and disorders such as Alzheimer's disease, Trisomy 21 (Down's Syndrome), Hereditary Cerebral Hemorrhage with Amyloidosis of the Dutch-type (HCHWA-D), and other neurodegenerative disorders. Such methods generally involve administering to a patient suspected of suffering from or being susceptible to the disease or injury an effective amount of a compound of formula I. Also according to the present invention there is provided a method of treating Alzheimer's disease and related senile dementia's in humans or other mammals which comprises administering to a human or other mammal an effective amount of a compound of the present invention.

The present invention also provides a method for the treatment of a disorder related to or associated with excessive BACE activity in a patient in need thereof which comprises providing said patient a therapeutically effective amount of at least one compound of formula I. Representative disorders include Alzheimer's disease, cognitive impairment, Down's Syndrome, HCHWA-D, cognitive decline, senile dementia, cerebral amyloid angiopathy, degenerative dementia, or other neurodegenerative disorders. Certain of these diseases are characterized by production of β-amyloid deposits or neurofibrillary tangles.

The present invention also provides methods for modulating (and, preferably, inhibiting) the activity of BACE, comprising administering to a patient and/or contacting a receptor thereof with an effective amount of at least one compound of Formula I. Certain methods further comprise determining BACE activity, either before or after said contacting step.

The present invention also provides methods of ameliorating β-amyloid deposits in a mammal, comprising administering to said mammal an effective amount of at least one compound of Formula I. Further methods ameliorate neurofibrillary tangles in a mammal, and comprise administering to said mammal an effective amount of at least one compound of Formula I.

FLOW DIAGRAM V

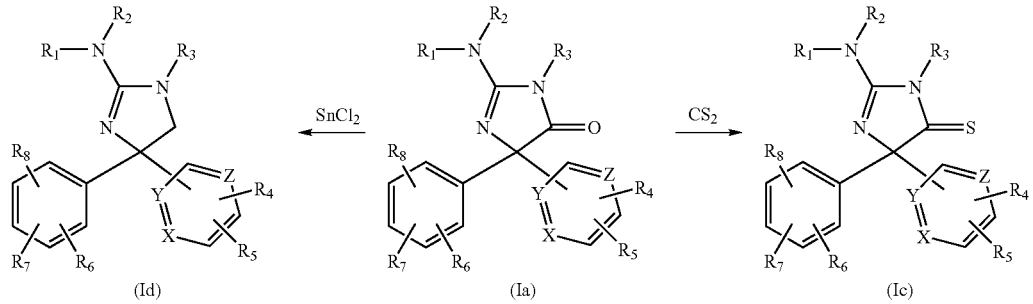

Advantageously, the compounds of formula I act as BACE inhibitors for the treatment of β-amyloid deposits and neurofibrillary tangles associated with such diseases as Alzheimer's disease, Trisomy 21 (Down's Syndrome), Hereditary Cerebral Hemorrhage with Amyloidosis of the Dutch-type (HCHWA-D), and other neurodegenerative disorders. Accordingly, the present invention provides methods for Also provided are methods of ameliorating symptoms of Alzheimer's disease, cognitive impairment, Down's Syndrome, HCHWA-D, cognitive decline, senile dementia, cerebral amyloid angiopathy, degenerative dementia, or other neurodegenerative disorders in a mammal, comprising administering to said mammal an effective amount of at least one compound of Formula I.

Further methods prevent Alzheimer's disease, cognitive impairment, Down's Syndrome, HCHWA-D, cognitive decline, senile dementia, cerebral amyloid angiopathy, degenerative dementia, or other neurodegenerative disorders in a mammal that is known to suffer from or suspected to be at risk of suffering from such diseases. These methods comprise administering to said mammal an amount of at least one compound of Formula I that is effective to prevent such disease.

As used in accordance with this invention, the term "providing," with respect to providing a compound or substance covered by this invention, means either directly administering such a compound or substance, or administering a prodrug, derivative, or analog which will form the effective amount of the compound or substance within the body. This invention also covers providing the compounds of this invention to treat the disease states disclosed herein that the compounds are useful for treating.

The term "patient", as used herein, refers to a mammal, preferably a human.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The terms "effective amount", "therapeutically effective amount" and "effective dosage" as used herein, refer to the amount of a compound that, when administered to a patient, is effective to at least partially ameliorate (and, in preferred embodiments, cure) a condition from which the patient is suspected to suffer.

It is understood that the effective dosage of the active compounds of this invention may vary depending upon the particular compound utilized, the mode of administration, the condition, and severity thereof, of the condition being treated, as well as the various physical factors related to the individual being treated. For treating Alzheimer's disease and other related senile dementia's, generally, satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg preferably from about 3.5 to about 5 mg. In the case of a 70 kg human adult, the total daily dose will generally be from about 7 mg to about 70 mg and may be adjusted to provide the optimal therapeutic result. This regimen may be adjusted to provide the optimal therapeutic response.

In one aspect, the present invention is directed to compositions comprising one or more compounds of formula I and one or more pharmaceutically acceptable carriers.

The present invention also comprises pharmaceutical compositions comprising compounds of the above-described Formula I and a pharmaceutically acceptable carrier.

The term "carrier", as used herein, shall encompass carriers, excipients, and diluents. Examples of carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulisifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, thransdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is incorporated by reference in its entirety.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The term NMR designates nuclear magnetic resonance. The terms TEA, DMSO and DMF designate triethyl amine, dimethyl sulfoxide and N,N-dimethylformamide, respectively. The terms DME and TBAF designate ethylene glycol dimethyl ether and tetrabutylamminium fluoride, respectively. The term TLC designates thin layer chromatography. The term NMR designates proton nuclear magnetic resonance and the term MS designates mass spectroscopy with (+) referring to the positive mode which generally gives a M+1 (or M+H) absorption where M=the molecular mass. All compounds are analyzed at least by MS and NMR.

Proton nuclear magnetic resonance spectra were obtained on a Bruker AVANCE 300 spectrometer at 300 MHz or a VARIAN 400 spectrometer at 400 MHz. Spectra are given in ppm (δ) and coupling constants, J values, are reported in Hertz. Tetramethylsilane was used as an internal reference standard. Infrared spectra were obtained on a Nicolet Nexus 470 (ATR) spectrometer. Mass spectra were obtained on a Perkin Elmer Sciex 100

EXAMPLE 1

Preparation of Trimethylsilyl-4-alkynylpyridine

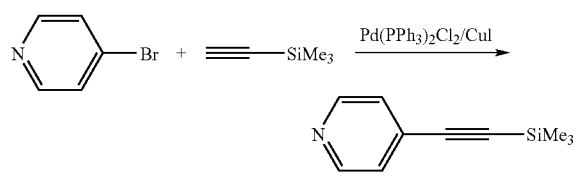

To a solution of 4-bromopyridine hydrochloride (5.0 g, 20.9 mmol) in DMF (80 mL) are added dichlorobis(triphenylphosphine)palladium (0.44 g, 0.63 mmol), copper iodide (0.097 g, 0.43 mmol), TEA (14.60 mL, 104.5 mL) and ethynyl(trimethyl)silane (4.43 mL, 31.35 mmol). The reaction mixture is heated at 65° C. for 3 h, cooled and quenched with H$_2$O (200 mL). The aqueous is extracted with EtOAc (3×70 mL). The combined organic extracts are washed with brine (80 mL), dried (MgSO$_4$), and concentrated. The crude material is purified by chromatography (silica gel, EtOAc/hexane: 15/85) to afford the title compound (3.24 g, 89%) as an oil. MS (+) ES: 176 (M+H)$^+$.

EXAMPLE 2

Preparation of 4-Ethynylpyridine

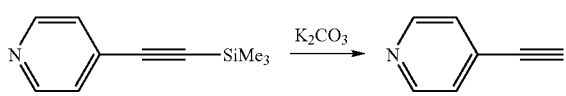

To a solution of trimethylsilyl-4-alkynylpyridine (6.00 g, 34.0 mmol) in MeOH (80 mL) is added solid K$_2$CO$_3$ (4.7 g, 34.0 mmol) at room temperature. After stirring for 2 h, the reaction mixture is diluted with Et$_2$O. The insoluble materials are removed by filtration (pass through a thin layer of silica gel), and washed with Et$_2$O. The filtrate is concentrated to dryness to give the title compound (2.56 g 73%) as a solid. Mp: 110-112° C.; MS (+) EI: 130 M$^+$.

EXAMPLE 3

Preparation of (1,1'-Biphenyl-3-ylethynyl)(trimethyl)silane

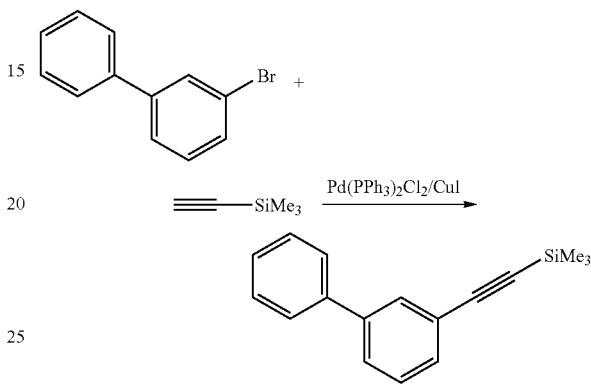

To a solution of 3-bromo-1,1'-biphenyl (5.06 g, 21.76 mmol) in TEA (20 mL) are added dichlorobis(triphenylphosphine)palladium (0.47 g, 0.65 mmol), copper iodide (0.08 g, 0.44 mmol) and ethynyl(trimethyl)silane (4.62 mL, 32.64 mmol). The reaction mixture is refluxed for 3 h and cooled to room temperature. After evaporation of the solvent, the crude material is purified by chromatography (silica gel, 100% hexane) to afford the title compound (4.81 g, 88%) as an oil. MS (+) EI: 250 M$^+$.

EXAMPLE 4

Preparation of 3-Ethynyl-1,1'-biphenyl

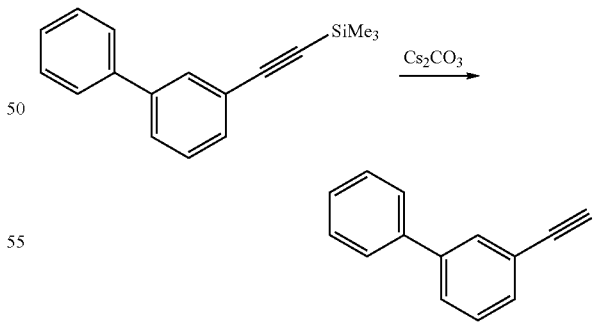

To a solution of (1,1'-biphenyl-3-ylethynyl)(trimethyl)silane (4.74 g, 18.96) in 1/1 EtOH/CH$_2$Cl$_2$ (60 mL) is added Cs$_2$CO$_3$ (6.78 g, 20.85 mmol) at room temperature. After stirring for 1 h, the insoluble material is filtered off and the filtrate is concentrated. The crude material is purified by chromatography (silica gel, 100% hexane) to give the title compound (3.07 g, 91%) as an oil. MS (+) EI: 178 M$^+$.

EXAMPLE 5

Preparation of 4-Bromo-2-methylpyridine

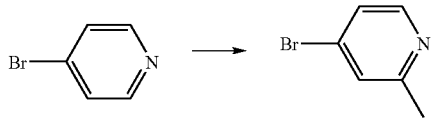

To a cooled (−78° C.) suspension of 4-bromopyridine hydrochloride (5.0 g, 25.7 mmol) in anhydrous THF (90 mL) was added dropwise a solution of MeMgCl (3.0 M in THF, 21 mL, 63.0 mmol). After addition, the reaction mixture was stirred at −78° C. for 15 min. Phenyl chloroformate (3.8 mL, 30 mmol) in THF (10 mL) was added slowly and the mixture was allowed to warm to room temperature. The reaction was quenched with saturated $NH_4Cl$ at 0° C. and extracted with $Et_2O$. The combined organic extracts were washed successively with $H_2O$, aqueous 1 N HCl and $H_2O$, dried ($MgSO_4$) and concentrated. The residue was dissolved in andydrous toluene (100 mL) and a solution of o-chloranil (7.8 g, 32 mmol) in glacial AcOH (60 mL) was added dropwise and the mixture was stirred for 22 h. a red suspension was formed and was made basic using 10% NaOH until a black emulsion was obtained. The mixture was filtered through Celite and washed with $H_2O$. The organic layer was extracted three times with aqueous 1 N HCl. The aqueous layers were basified with aqueous 50% NaOH and extracted with $CH_2Cl_2$. The combined organic extracts were dried ($MgSO_4$) and the solvent was removed under vacuum to give the title compound (2.35 g, 53%) as an oil. MS (+) EI: 171 $M^+$.

EXAMPLE 6

Preparation of 4-(Phenylethynyl)pyridine

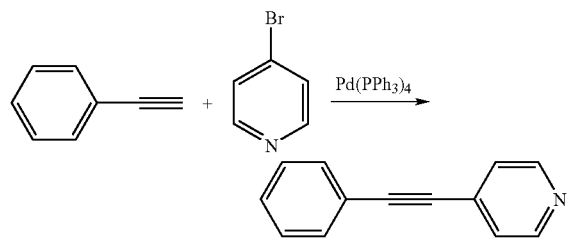

To a suspension of 4-bromopyridine hydrochloride (3.9 g, 20 mmol), tetrakis(triphenylphosphine)palladium (2.32 g, 2.0 mmol), triethylamine (16.8 mL, 120 mmol) in dry DMF (150 mL) is added phenylacetylene (4.2 mL, 40 mmol) at room temperature. After stirring for 3 hours at 80° C., the reaction mixture is concentrated. The residue is dissolved in $CH_2Cl_2$ (100 mL), washed with $H_2O$, brine (50 mL), dried ($MgSO_4$) and concentrated. The crude material is purified by chromatography (silica gel, EtOAc/hexane: 10/90) to afford the title compound as a solid (3.25 g, 91%). Mp 51-53° C. MS (+) ES: 180 $(M+H)^+$.

EXAMPLE 7

Preparation of 3-(Phenylethynyl)pyridine

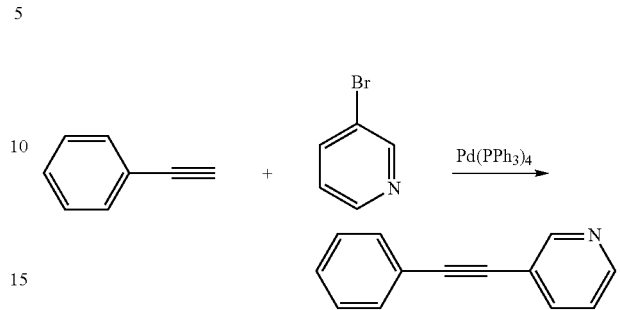

The title compound is prepared by using essentially the same procedure as in Example 6 affording a solid (95%). Mp: 42-43° C. MS (+) ES: 180 $(M+H)^+$.

EXAMPLE 8

Preparation of 4-[(3-Bromophenyl)ethynyl]pyridine

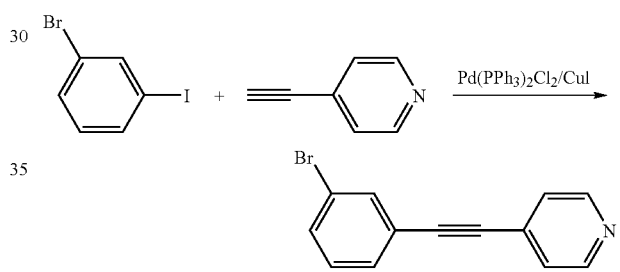

The title compound is prepared by using essentially the same procedure as Example 1 affording a solid (87%). Mp: 140-142° C. MS (+) ES: 257 $(M+H)^+$.

EXAMPLE 9

Preparation of 4-[(3-Methoxyphenyl)ethynyl]pyridine

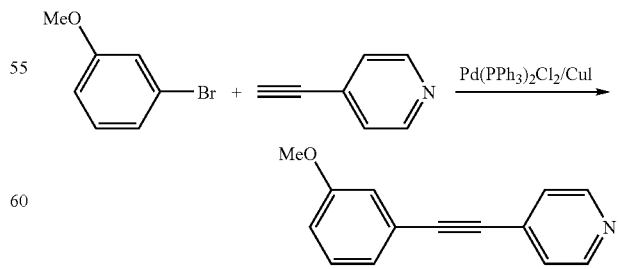

The title compound is prepared by using essentially the same procedure as Example 1 affording a solid (87%). Mp: 33-35° C. MS (+) ES: 220 $(M+H)^+$.

EXAMPLE 10

Preparation of 4-(1,1'-Biphenyl-3-ylethynyl)pyridine

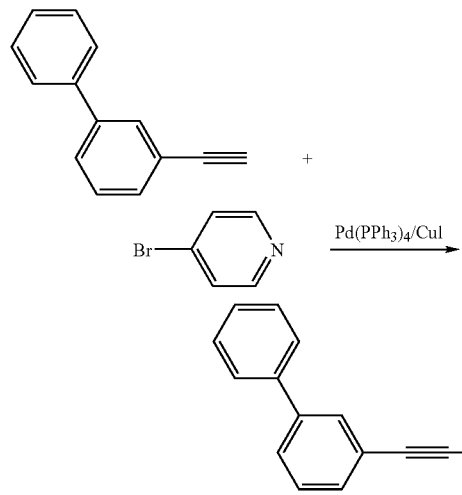

To a solution of 4-ethynyl-1,1'-biphenyl (3.4 g, 19.1 mmol) in DMF (30 mL) are added 4-bromopyridine hydrochloride (3.63 g, 18.73 mmol), tetrakis(triphenyl-phosphine)palladium (0.65 g, 0.56 mmol), copper iodide (0.07 g, 0.37 mmol) and TEA (10 mL) at room temperature. After stirring for 3 h at 65° C., the reaction mixture is cooled to room temperature and the insoluble material is filtered off. To the filtrate is added water. The aqueous is extracted with Et$_2$O (2×150 mL). The combined organic extracts are washed with water, 10% aqueous LiCl (50 mL), brine, dried (MgSO$_4$) and concentrated on a rotary evaporator. The crude material is purified by chromatography (silica gel, EtOAc/hexane: 20/80) to afford the title compound (4.2 g, 88%) as an oil. MS (+) ES: 279 (M+Na)$^+$.

EXAMPLE 11

Preparation of 4-(1,1'-Biphenyl-3-ylethynyl)-2-methylpyridine

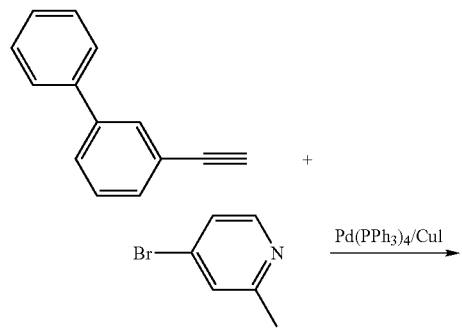

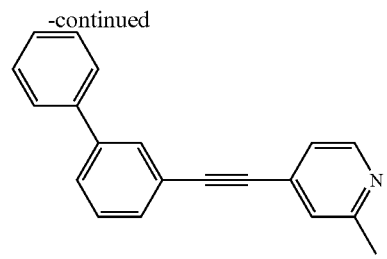

The title compound is prepared by using essentially the same procedure as Example 10 affording solid (59%). Mp: 56-58° C. MS (+) ES: 270 (M+H)$^+$.

EXAMPLE 12

Preparation of 3-(1,1'-Biphenyl-3-ylethynyl)pyridine

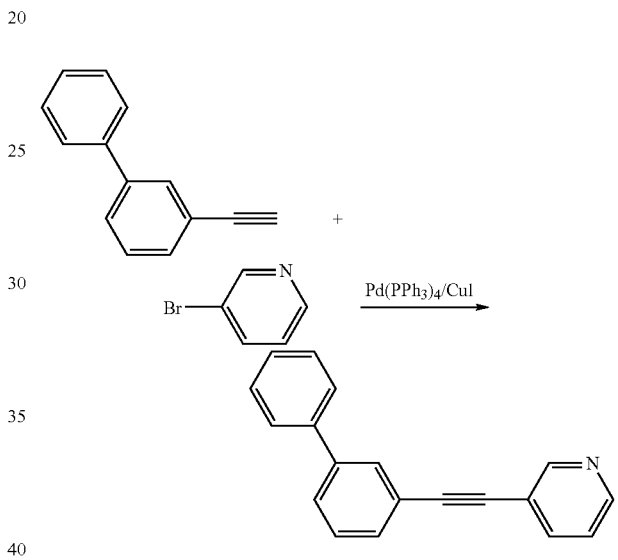

The title compound is prepared by using essentially the same procedure as Example 10 affording an oil (41%). MS (+) ES: 256 (M+H)$^+$.

EXAMPLE 13

Preparation of 4-[(3'-fluoro-1,1'-Biphenyl-3-yl)ethynyl]pyridine

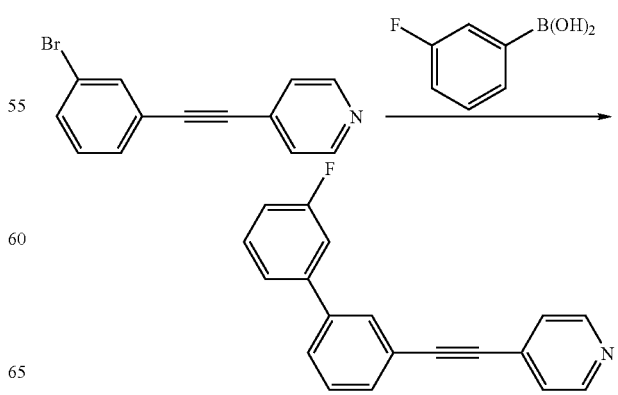

To a solution 4-[(3-bromophenyl)ethynyl]pyridine (220 mg, 0.85 mmol) in DME is added 3-fluorophenylbronic acid (237 mg, 1.70 mmol), tetrakis(triphenylphosphine)palladium (98 mg, 0.085 mmo) and 2.0M aqueous sodium carbonate (1.70 mL, 3.40 mmol) at room temperature. After refluxing for 3 hour, the reaction mixture is cooled, quenched with saturated sodium carbonate (10 mL), diluted with EtOAc (30 mL). The two layers are separated and the aqueous layer is extracted with EtOAc (20 mL). The combined organic extracts are washed with brine (20 mL), dried (MgSO4) and concentrated on a rotary evaporator. The crude mixture is purified by chromatography (silica gel, EtOAc/hexane: 30/70) to give the title compound (141 mg, 61%) as an oil. MS(+) ES: 274 (M+H)$^+$.

EXAMPLES 14-15

Preparation of 4-{[3'-Substituted-1,1'-biphenyl-3-yl]ethynyl}pyridine

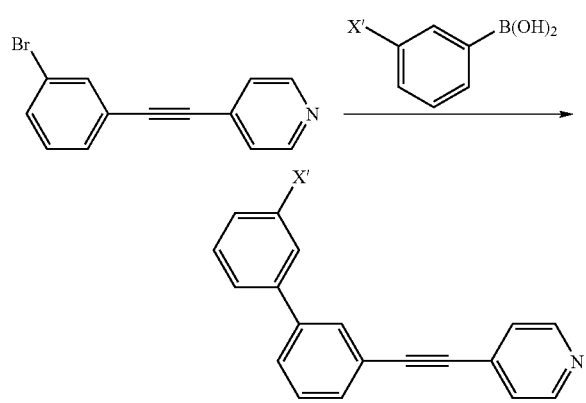

Using essentially the same procedure described in Example 13 and employing the appropriated bronic acid, the compounds shown in Table I are obtained and identified by NMR and mass spectral analyses.

TABLE I

| Example | X' | mp (° C.) | M + H |
|---|---|---|---|
| 14 | OCF$_3$ | oil | 340 |
| 15 | CN | 126-128 | 281 |

EXAMPLE 16

Preparation of 2-[3-(Pyridin-4-ylethynyl)phenyl]pyrazine

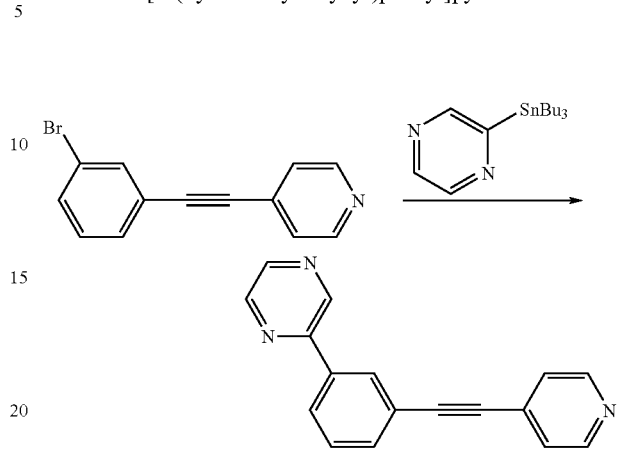

To a solution of 4-[(3-bromophenyl)ethynyl]pyridine (387 mg, 1.50 mmol) in toluene (10 mL) is added tetrakis(triphenylphosphine)palladium (87 mg, 0.075 mmol) and 2-(tributylstannyl)pyrazine (1.45 g, 3.75 mmol) at room temperature. After refluxing for 24 h, the reaction mixture is cooled and diluted with EtOAc (100 mL), washed with saturated NaHCO$_3$ (2×30 mL), brine (30 mL), dried over MgSO$_4$ and concentrated on a rotary evaporator. The crude material is purified by chromatography (silica gel, EtOAc/hexane: 40/60 to give the title compound (153 mg, 40%) as solid. mp: 94-95° C. MS(+) ES: 258 (M+OH)$^+$.

EXAMPLE 17

Preparation of 1-Phenyl-2-pyridin-4-ylethane-1,2-dione

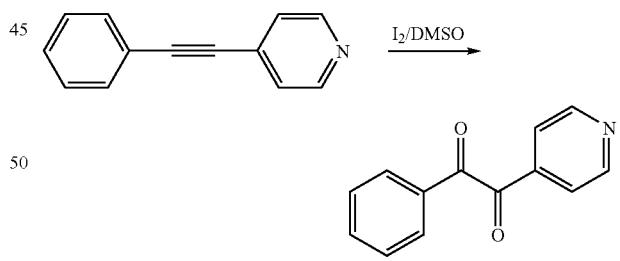

A solution of 4-(phenylethynyl)pyridine (2.25 g, 12.6 mmol) and powder iodine (1.60 g, 6.3 mmol) in DMSO (30 mL) is heated at 155° C. for 4 h. The reaction mixture is cooled and poured to H$_2$O (100 mL). The aqueous is neutralized with powdered Na$_2$CO$_3$ to pH~12 and extracted with EtOAc (2×100 mL). The combined organic extracts are washed sequentially with H$_2$O (60 mL) and brine (60 mL), then dried and concentrated. The crude material is purified by chromatography (silica gel: EtOAc/hexane: 20/80) to afford the title compound (0.81 g, 30%) as an oil. MS (+) ES: 212 (M+H)$^+$.

EXAMPLE 18

Preparation of 1-(3-Bromophenyl)-2-pyridin-4-ylethane-1,2-dione

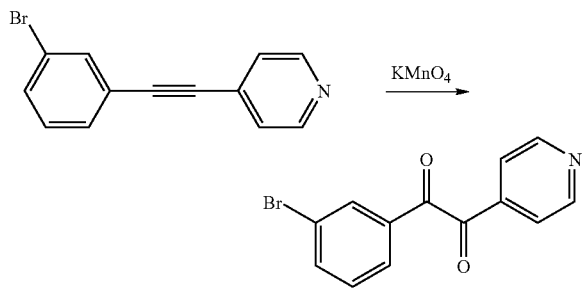

To a solution of 4-[(3-bromophenyl)ethynyl]pyridine (1.81 g, 7.0 mmol) in acetone (63 mL) is added a warm (~40° C.) solution of NaHCO$_3$ (0.35 g, 4.20 mmol) and MgSO$_4$ (1.26 g, 10.50 mmol) in H$_2$O (63 mL) followed by the addition of solid potassium permanganate (2.43 g, 15.40 mmol) in one portion. After stirring at room temperature for 4 minutes, the reaction mixture is extracted with 1/1 Et$_2$O/hexane. The extracts are combined, dried over MgSO$_4$ and concentrated to dryness to afford the title compound (1.52 g, 75%) as a solid. Mp: 88-90° C. MS (+) ES: 289 (M+H)$^+$.

EXAMPLES 19-22

Preparation of 1-(3-bromophenyl)-2-pyridin-4-ylethane-1,2-dione

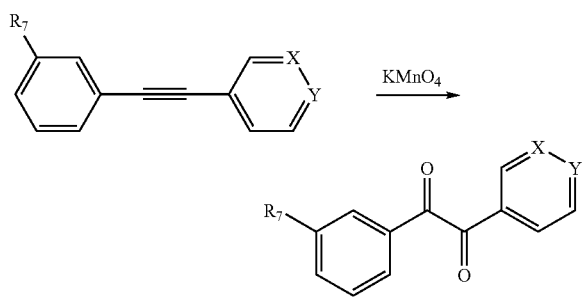

Using essentially the same procedures described in Examples 17 and 18 and employing the appropriate alkyne substrate, the compounds shown in Table II are obtained and identified by NMR and mass spectral analyses.

TABLE II

| Example | R7 | X | Y | mp (° C.) | M + H |
|---|---|---|---|---|---|
| 19 | OCH$_3$ | CH | N | 71-73 | 242 |
| 20 | C$_6$H$_5$ | CH | N | 74-76 | 288 |

TABLE II-continued

| Example | R7 | X | Y | mp (° C.) | M + H |
|---|---|---|---|---|---|
| 21 | C$_6$H$_5$ | N | CH | oil | — |
| 22 | H | N | CH | oil | 212 |

EXAMPLE 23

Preparation of 2-Amino-3-methyl-5-phenyl-5-pyridin-4-yl-3,5-dihydro-4H-imidazol-4-one

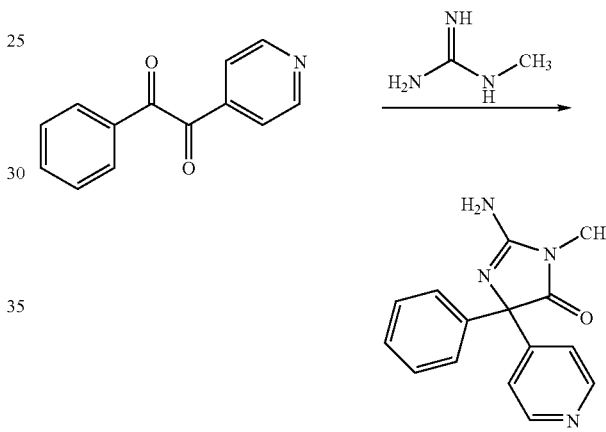

A suspension of 1-phenyl-2-pyridin-4-ylethane-1,2-dione (0.81 g, 3.8 mmol), N-methylguanidine hydrochloride (1.92 g, 17.5 mmol) and Na$_2$CO$_3$ (3.71 g, 35 mmol) in EtOH (25 mL) and H$_2$O (5 mL) is refluxed for 18 h. The reaction mixture is cooled and poured into water. The precipitate is collected by filtration, washed with water, and air-dried to give the title compound (0.62 g, 62%) as a solid. Mp 154-155° C. MS (+) ES: 267 (M+H)$^+$.

EXAMPLES 24-29

Preparation of 2-Amino-5-(substituted-phenyl)-3-methyl-5-pyridinyl-3,5-dihydro-4H-imidazol-4-one Compounds

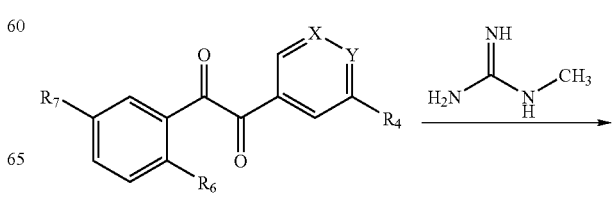

-continued

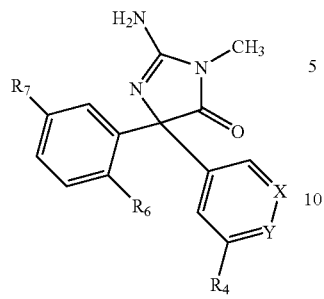

Using essentially the same procedure described in Example 23 and employing the appropriate diketone, the compounds shown in Table III were obtained and identified by NMR and mass spectral analyses.

TABLE III

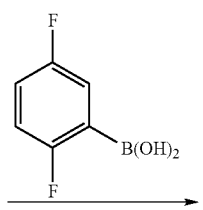

| Ex. No. | R4 | R6 | R7 | X | Y | mp (° C.) | M + H |
|---|---|---|---|---|---|---|---|
| 24 | H | H | OCH₃ | CH | N | 202-204 | 297 |
| 25 | H | H | Br | CH | N | 253-255 | 344 |
| 26 | H | H | C₆H₅ | CH | N | 216-218 | 343 |
| 27 | H | H | C₆H₅ | N | CH | 212-214 | 343 |
| 28 | H | H | H | N | CH | 205-206 | 267 |
| 29 | CH(CH₃)₂ | F | F | H | N | 193-195 | 421 |

EXAMPLE 30

Preparation of 2-Amino-5-(2',5'-difluoro-1,1'-biphenyl-3-yl)-3-methyl-5-pyridin-4-yl-3,5-dihydro-4H-imidazol-4-one

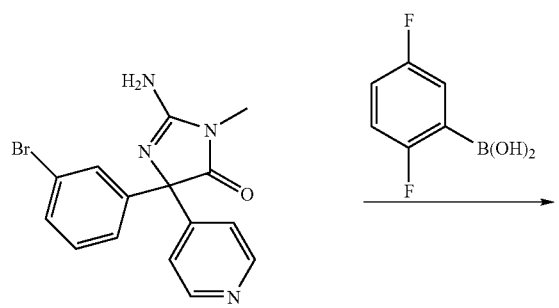

-continued

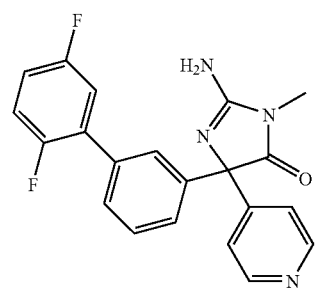

To a solution of 2-amino-5-(3-bromophenyl)-3-methyl-5-pyridin-4-yl-3,5-dihydro-4H-imidazol-4-one (104 mg, 0.3 mmol) in DME (5 mL) is added 2,5-difluorophenylboronic acid (96 mg, 0.6 mmol), tetrakis(triphenylphosphine)palladium (35 mg, 0.03 mmo) and 2.0M aqueous sodium carbonate (0.6 mL, 1.2 mmol) at room temperature. The reaction mixture is refluxed for 1 hour and cooled. After evaporation of the solvent, the crude mixture is purified by chromatography (silica gel, EtOAc/2M methanolic NH₃: 92/8) to give the title compound (95 mg, 84%) as a solid. mp: 200-202° C.; MS(+) ES: 379 (M+H)⁺.

EXAMPLES 31-50

Preparation of 2-Amino-5-(3-substitutedphenyl)-3-methyl-5-pyridin-4-yl-3,5-dihydro-4H-imidazol-4-one Compounds

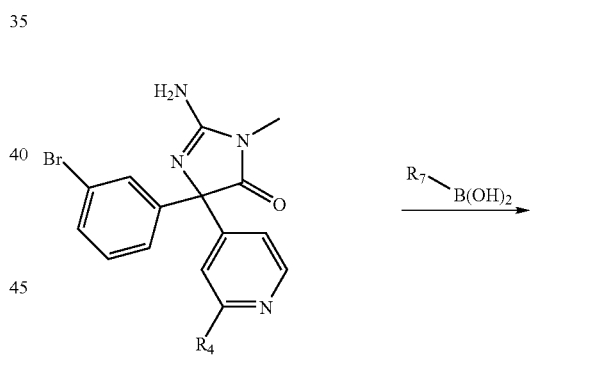

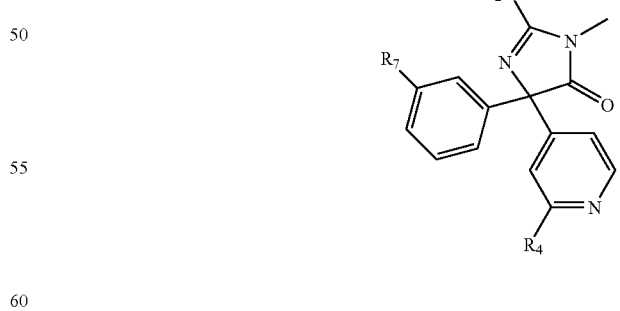

Using essentially the same procedure described in Example 30 and employing the appropriate boronic acid and aminohydantoin starting materials, the compounds shown in Table IV were obtained and identified by NMR and mass spectral analyses.

TABLE IV

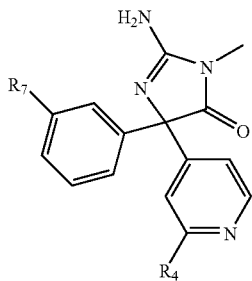

| Ex. No. | R7 | R4 | mp (° C.) | M + H |
|---|---|---|---|---|
| 31 | 3,5-difluorophenyl | H | 195-195 | 379 |
| 32 | 3-(trifluoromethyl)phenyl | H | 234 | 411 |
| 33 | 5-methoxypyridin-3-yl | H | 198-200 | 374 |
| 34 | 3-methoxylphenyl | H | 176-178 | 373 |
| 35 | 3-hydroxylphenyl | H | 263-265 | 359 |
| 36 | 3-(hydroxymethyl)phenyl | H | 177-179 | 373 |
| 37 | 3-(aminocarbonyl)phenyl | H | 188-190 | 386 |
| 38 | 3-acetylphenyl | H | 218-220 | 385 |
| 39 | 5-fluoro-2-methoxyphenyl | H | 233-235 | 391 |
| 40 | 2,3-difluorophenyl | H | 181-183 | 379 |
| 41 | 5-cyano-2-fluorophenyl | H | 213-215 | 384* |
| 42 | 2-chloro-5-fluoropyridin-3-yl | H | 120-122 | 396 |
| 43 | 2-fluoropyridin-3-yl | H | 234-236 | 362 |
| 44 | pyridin-3-yl | H | — | — |
| 45 | 3-furyl | H | 113-115 | 333 |
| 46 | 3-thienyl | H | 217-219 | 349 |
| 47 | 1H-pyrazol-3-yl | H | 148-150 | 333 |
| 48 | 1-methyl-1H-pyrazol-3-yl | H | 199-201 | 347 |
| 49 | 2-methoxypyridin-3-yl | H | 243-245 | 374 |
| 50 | 5-cyano-2-thienyl | H | 220-222 | 374 |

*[M − H]−

EXAMPLE 51

Preparation of 2-Amino-5-(3-hydroxyphenyl)-3-methyl-5-pyridin-4-yl-3,5-dihydro-4H-imidazol-4-one

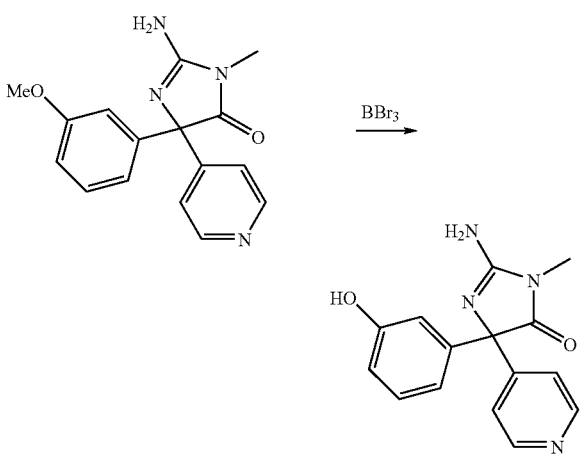

To a suspension of 2-amino-5-(3-methoxyphenyl)-3-methyl-5-pyridin-4-yl-3,5-dihydro-4H-imidazol-4-one (0.75 g, 2.5 mmol) in CH$_2$Cl$_2$ (7.5 mL) is added BBr$_3$ (1.0 M in CH$_2$Cl$_2$, 15 mL, 15 mmol) at −78° C. After addition, the reaction mixture is warmed to room temperature and stirred for 3 h. The reaction mixture is poured into ice-water (50 mL) and the two layers are separated. The aqueous is neutralized with 50% aqueous NaOH to pH∼7 and extracted with 4/1 CH$_2$Cl$_2$/2-PrOH (3×100 mL). The combined organic extracts are washed with brine (150 mL), dried (Na$_2$SO$_4$) and concentrated. The resultant residue is purified by chromatography (silica gel, EtOAc/2M methanolic NH$_3$: 95/5) to give the title compound (0.58 g, 79%) as a solid. Mp: 245-247° C.; MS(+) ES: 283 (M+H)$^+$.

EXAMPLE 52

Preparation of 2-Amino-3-methyl-5-(3-propoxyphenyl)-5-pyridin-4-yl-3,5-dihydro-4H-imidazol-4-one

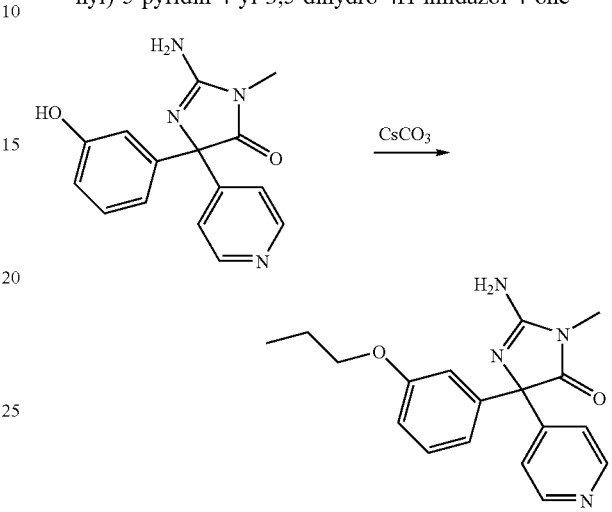

To a stirred solution of 2-amino-5-(3-hydroxyphenyl)-3-methyl-5-pyridin-4-yl-3,5-dihydro-4H-imidazol-4-one (0.13 g, 0.46 mmol) in acetone (20 mL) and DMF (1 mL) is added 1-iodopropane (0.07 mL, 0.69 mmol) and Cs$_2$CO$_3$ (1.50 g, 4.60 mmo). After refluxed for 1 hour, the solvent is evaporated and the crude material was purified by chromatography (silica gel, EtOAc/2M methanolic NH$_3$: 97/3) to give the title compound (0.145 g, 97%) as a solid. mp: 173-175° C.; MS(+) ES: 325 (M+H)$^+$.

EXAMPLES 53-67

Preparation of 2-Amino-5-(substituted-phenyl)-3-methyl-5-pyridinyl-3,5-dihydro-4H-imidazol-4-one Compounds

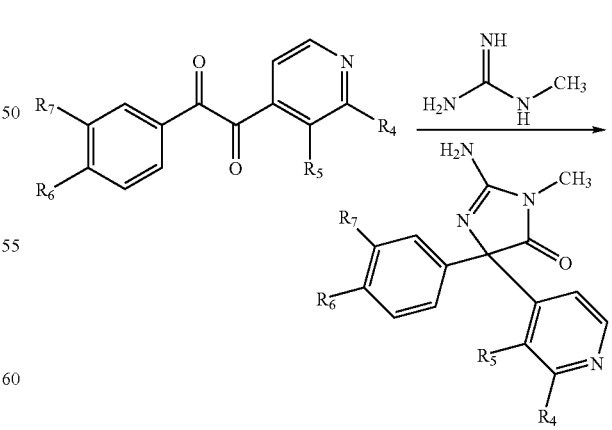

Using essentially the same procedure described in Example 23 and employing the appropriate diketone, the compounds shown in Table V were obtained and identified by NMR and mass spectral analyses.

TABLE V

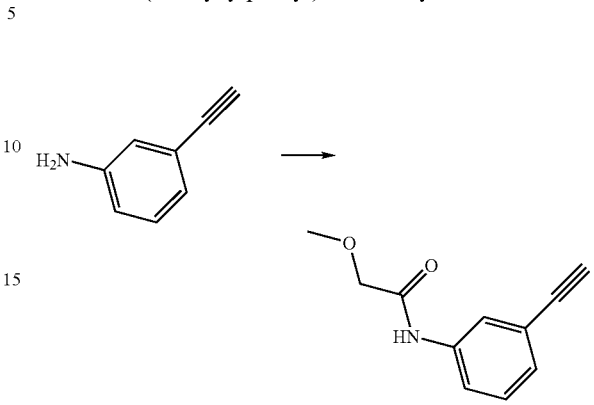

| Ex. No. | R4 | R5 | R6 | R7 | mp (° C.) | [M + H] |
|---|---|---|---|---|---|---|
| 53 | H | H | H | 3-fluorophenyl | 143-145 | 361 |
| 54 | H | H | H | 3-(trifluoromethoxy)phenyl | 208-210 | 427 |
| 55 | H | H | H | 3-cyanophenyl | 233-235 | 366 |
| 56 | H | H | H | 3-pyrazin-2-yl | 228-230 | 345 |
| 57 | CH₃ | H | H | phenyl | 178-180 | 355 |
| 58 | H | F | H | 2-fluoropyridin-3-yl | 237-238 | 380 |
| 59 | H | H | F | 2-fluoropyridin-3-yl | 218-220 | 380 |
| 60 | CH₃ | H | H | pyridin-3-yl | 230-231 | 358 |
| 61 | CH₃ | H | H | pyrimidin-5-yl | 137-139 | 359 |
| 62 | CH₃ | H | H | 2,5-difluorophenyl | 161-163 | 393 |
| 63 | C₂H₅ | H | H | pyridin-3-yl | 217-219 | 372 |
| 64 | C₂H₅ | H | H | pyrimidin-5-yl | 177-179 | 373 |
| 65 | C₂H₅ | H | H | 2,5-difluorophenyl | 188-192 | 407 |
| 66 | CH₃ | H | H | pyrazin-2-yl | 138-141 | 359 |
| 67 | C₂H₅ | H | H | pyrazin-2-yl | 138-140 | 373 |

EXAMPLE 68

Preparation of 1-(cyclopropylmethoxy)-3-ethynylbenzene

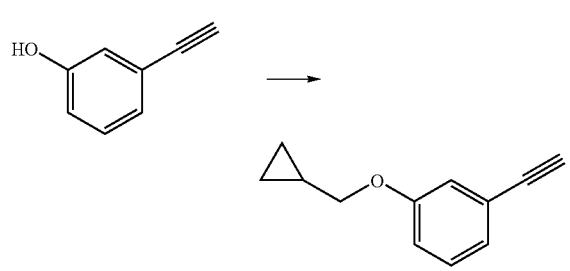

To a solution of 3-ethynylphenol (1.18 g, 10.0 mmol) in acetone (30 mL) is added (bromomethyl)cyclopropane (1.02 mL, 10.0 mmol), sodium iodide (0.75 g, 5.0 mmol) and Cs₂CO₃ (6.52 g, 20.0 mmol) at room temperature. After refluxing over night, the reaction mixture is cooled, diluted with Et₂O (300 mL) and pass through a thin layer of silica gel. The solution is concentrated. The resultant residue is purified by chromatography (silica gel, EtOAc/hexane: 1/99) to give the title compound (1.45 g, 84%) as an oil. MS(+) APPI: 173 (M+H)⁺.

EXAMPLE 69

Preparation of N-(3-Ethynylphenyl)-2-methoxyacetamide

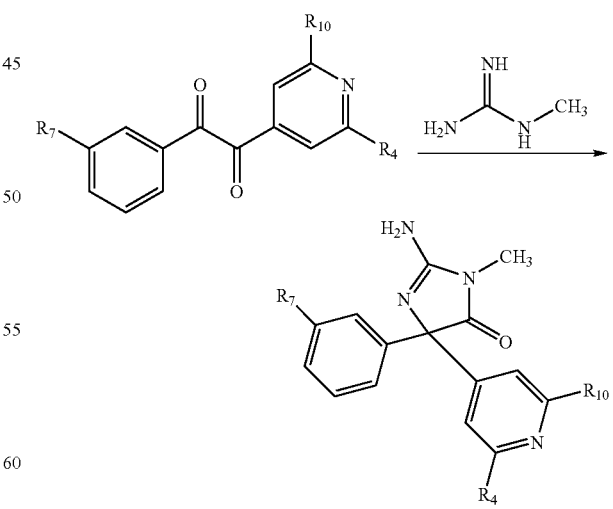

To a cooled solution of 3-ethynylphenylamine (7.02 g, 60 mmol) in methylene chloride is added a solution of methoxyacetyl chloride (7.8 g, 72 mmol) in methylene chloride (10 mL) dropwise over a period of 30 min at 0° C. After addition, the reaction mixture is allowed to warm-up to room temperature and stirred overnight. The solvent is evaporated and the residue is partitioned between water and ethyl acetate. The organic phase is washed with saturated NaHCO₃, H₂O, dried (MgSO₄) and concentrated to afford the title compound as a colorless oil 10.2 g (90%). ¹HNMR (CDCl3): δ (ppm) 3.04 (s, 1H,), 3.48 (s, 3H), 3.98 (s, 2H), 7.24 (m, 2H), 7.61 (d, 1H), 7.66 (s, 1H), 8.21 (s, b, 1H).

EXAMPLES 70-82

Preparation of 2-Amino-5-(substituted-phenyl)-3-methyl-5-pyridinyl-3,5-dihydro-4H-imidazol-4-one Compounds

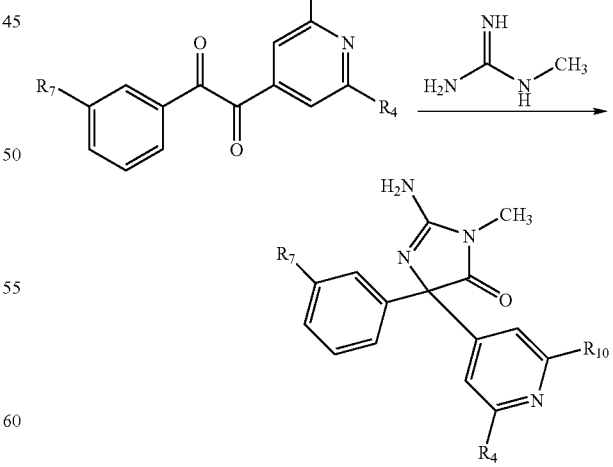

Using essentially the same procedure described in Example 23 and employing the appropriate diketone, the compounds shown in Table VI were obtained and identified by NMR and mass spectral analyses.

TABLE VI

| Ex. No. | R4 | R10 | R7 | mp (° C.) | [M + H] |
|---|---|---|---|---|---|
| 70 | C₂H₅ | C₂H₅ | 2-fluoropyridin-3-yl | 103-105 | 418 |
| 71 | H | H | cyclopropylmethoxy | 200-202 | 337 |
| 72 | C₂H₅ | C₂H₅ | cyclopropylmethoxy | 68-70 | 393 |
| 73 | H | H | NHCOCH₂OCH₃ | 92-93 | 394 |
| 74 | CH₃ | CH₃ | pyridin-3-yl | 176-180 | 372 |
| 75 | CH₃ | CH₃ | pyrimidin-5-yl | 199-203 | 373 |
| 76 | CH₃ | CH₃ | 2,5-difluorophenyl | 184-190 | 407 |
| 78 | CH₃ | C₂H₅ | Br | — | 387 |
| 79 | i-propyl | H | Br | — | 387 |
| 80 | i-propyl | CH₃ | Br | — | — |
| 81 | Cl | H | Br | — | 379 |
| 82 | C₂H₅ | C₂H₅ | Br | — | 401 |

TABLE VII

| Ex. No. | R4 | R10 | R6 | R7 | mp (° C.) | [M + H] |
|---|---|---|---|---|---|---|
| 83 | CH₃ | C₂H₅ | H | pyridin-3-yl | 135-139 | 386 |
| 84 | CH₃ | C₂H₅ | H | pyrimidin-5-yl | 152-155 | 387 |
| 85 | CH₃ | C₂H₅ | H | 2,5-difluorophenyl | 114-117 | 421 |
| 86 | CH₃ | C₂H₅ | H | pyrazin-2-yl | 130-134 | 387 |
| 87 | i-Pr | H | H | pyrimidin-5-yl | 145-147 | 387 |
| 88 | i-Pr | CH₃ | H | pyrimidin-5-yl | 135-139 | 401 |
| 89 | Cl | H | H | pyridin-3-yl | 223-225 | 378 |
| 90 | C₂H₅ | C₂H₅ | H | pyridin-3-yl | 152-157 | 400 |
| 91 | C₂H₅ | C₂H₅ | H | pyrimidin-5-yl | 205 | 401 |
| 92 | C₂H₅ | C₂H₅ | H | 2,5-difluorophenyl | 107-112 | 435 |
| 93 | C₂H₅ | C₂H₅ | H | 6-fluoropyridin-3-yl | — | 418 |
| 94 | C₂H₅ | C₂H₅ | F | pyrimidin-5-yl | 101-105 | 419 |
| 95 | C₂H₅ | C₂H₅ | F | 2-fluoropyridin-3-yl | 173-174 | 436 |
| 96 | C₂H₅ | C₂H₅ | F | 4-fluoropyridin-3-yl | — | — |

EXAMPLES 83-95

Preparation of 2-Amino-5-(substituted-phenyl)-3-methyl-5-(substituted-pyridinyl)-3,5-dihydro-4H-imidazol-4-one Compounds

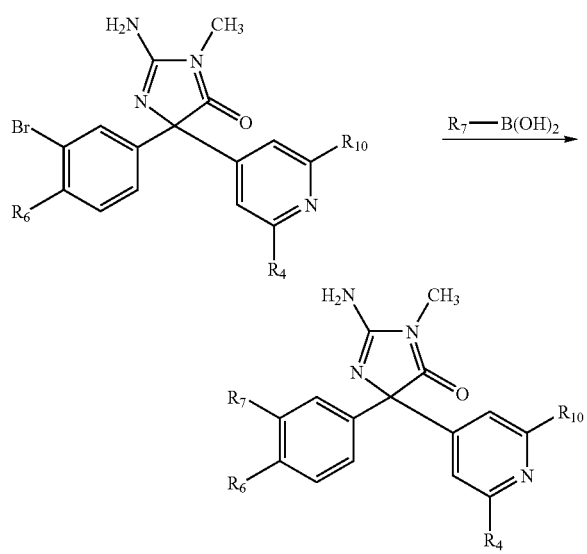

EXAMPLES 97-100

Preparation of 2-Amino-5-(substituted-phenyl)-3-methyl-5-(substituted-pyridinyl)-3,5-dihydro-4H-imidazol-4-one Compounds

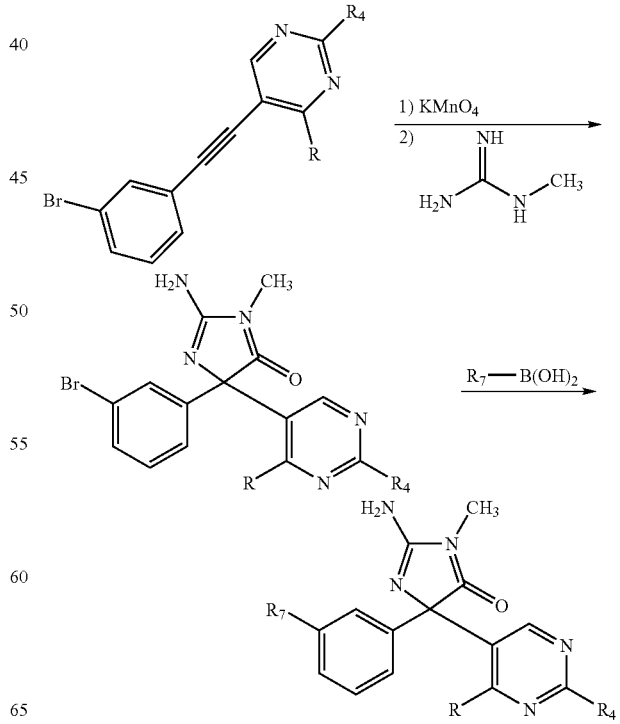

Using essentially the same procedure described in Example 30 and employing the appropriate boronic acid and suitable 5-(3-bromophenyl)imidazolone substrate, the compounds shown in Table VII were obtained and identified by NMR and mass spectral analyses. In Table VII, the term i-Pr designates isopropyl.

Using essentially the same procedures described in Examples 6, 17 and 30 and employing the appropriate boronic acid and suitable 5-(3-bromophenyl)-imidazolone substrate, the compounds shown in Table VIII were obtained and identified by NMR and mass spectral analyses.

TABLE VIII

| Ex. No. | R | R4 | R7 | mp (° C.) | MS m/z |
|---|---|---|---|---|---|
| 97 | OCH$_3$ | OCH$_3$ | pyrimidin-5-yl | glass | 406.2 |
| 98 | OCH$_3$ | OCH$_3$ | 2-fluoropyridin-3-yl | glass | 423.2 |
| 99 | H | OCH$_3$ | pyrimidin-5-yl | >230 | 376.2 |
| 100 | H | OCH$_3$ | 2-fluoropyridin-3-yl | 218-222 | 393.1 |

EXAMPLE 101

Preparation of 2-Amino-5-(2,6-dimethylpyridin-4-yl))-3-methyl-5-(3-pyrazin-2-ylphenyl))-3,5-dihydro-4H-imidazol-4-one

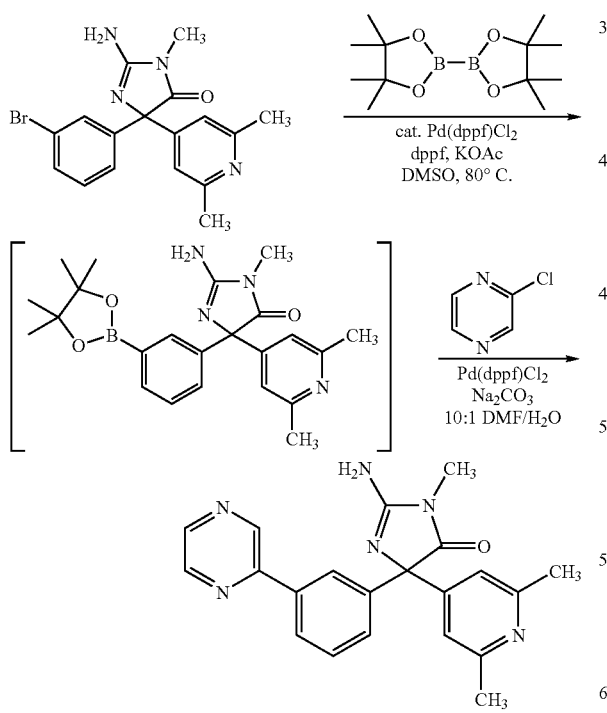

A mixture of 2-amino-5-(3-bromophenyl)-5-(2,6-dimethylpyridin-4-yl))-3-methyl-3,5-dihydro-4H-imidazol-4-one (0.176 g, 0.472 mmol), bis(pinacolato)diboron (0.134 g, 0.528 mmol), bis(diphenylphosphino)ferrocene-palladium(II) chloride (0.0135 g, 0.0165 mmol), diphenylphosphino ferrocene (0.009 g, 0.017 mmol) and potassium acetate (0.138 g, 1.41 mmol) in anhydrous dimethyl sulfoxide (1.0 mL) was heated at 80° C. for 17 h. The mixture was cooled to room temperature and diluted with ethyl acetate (50 mL) and brine (50 mL). The layers were separated, and the aqueous layer was extracted with ethyl acetate (2×25 mL). The combined organic extracts were dried over sodium sulfate, filtered and concentrated to afford the boronic ester intermediate (0.311 g crude, >quantitative) as a light yellow solid. A mixture of said boronic ester (0.31 g, approx. 0.47 mmol), bis(diphenylphosphino)-ferrocenepalladium(II) chloride (0.019 g, 0.0234 mmol), sodium carbonate (0.160 g, 1.5 mmol), DMF (8 mL) and water (0.8 mL) under nitrogen was treated with 2-chloropyrazine (0.0538 g, 0.47 mmol) and heated at 80° C. for 2.5 h. The mixture was cooled to room temperature, ethyl acetate (100 mL) and water (100 mL) were added, and the layers were separated. The aqueous layer was extracted with ethyl acetate and the combined organic layers were washed with 2% aqueous lithium chloride, dried over sodium sulfate, filtered, and concentrated. Purification of the resultant residue by flash chromatography (silica, 95:5:0.5 methylene chloride/methanol/concentrated ammonium hydroxide) afforded a residue which was further purified by semi-preparative HPLC to afford the title product (6.9 mg, 4%) as an off-white solid: $^1$H NMR (300 MHz, CDCl$_3$) δ 9.00 (d, J=1.4 Hz, 1H), 8.62 (dd, J=2.4, 1.6 Hz, 1H), 8.51 (d, J=2.5 Hz, 1H), 8.16 (d, J=1.5 Hz, 1H), 7.93 (dd, J=7.8, 1.2 Hz, 1H), 7.64 (d, J=8.0 Hz, 1H), 7.49 (t, J=7.8 Hz, 1H), 7.12 (s, 2H), 3.14 (s, 3H), 2.49 (s, 6H); ESI MS m/z 373 [C$_{21}$H$_{20}$N$_6$O+H]$^+$.

EXAMPLE 102

Preparation of 2-Amino-3-methyl-5-(2-methyl-1-oxidopyridin-4-yl)-5-(3-pyrimidin-5-ylphenyl))-3,5-dihydro-4H-imidazol-4-one

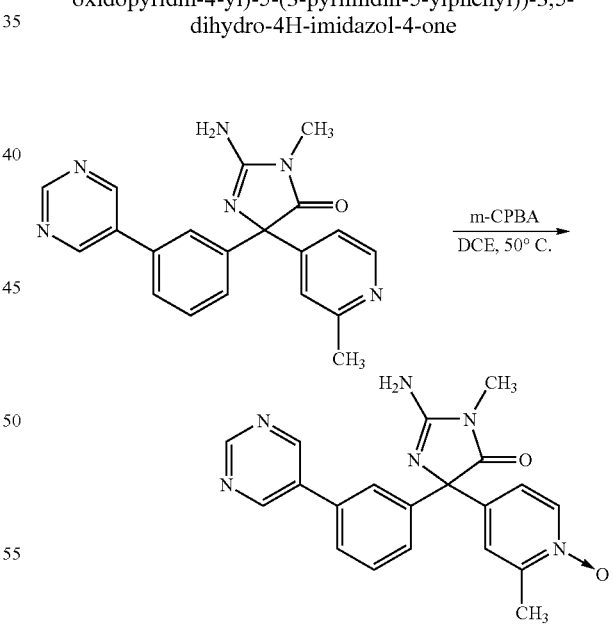

A mixture of 2-amino-3-methyl-5-(2-methylpyridin-4-yl)-5-(3-pyrimidin-5-ylphenyl))-3,5-dihydro-4H-imidazol-4-one (0.101 g, 0.282 mmol) in dichloroethane (2.0 mL) was treated with m-CPBA (0.057 g, 0.330 mmol) and heated at 50° C. under nitrogen for 45 min. Additional m-CPBA (0.10 g, 0.579 mmol) was then added and the mixture was stirred at 50° C. for an additional 30 min. After cooling to room temperature, the mixture was diluted with dichloromethane (60 mL) and 1 N NaOH (60 mL). The layers were separated and the aqueous layer was extracted with dichloromethane. The combined organic extracts were washed with brine, dried over sodium sulfate, filtered and concentrated. Purification of the residue by flash chromatography (silica, 93:7:0.5 to 90:10:0.5 methylene chloride/methanol/concentrated ammonium hydroxide) afforded the title product (0.014 g, 13%) as a white solid, mp 181-186° C.; $^1$H NMR (300 MHz, CDCl$_3$) δ 9.21 (s, 1H), 8.92 (s, 2H), 8.19 (d, J=6.8 Hz, 1H), 7.74 (s, 1H), 7.63 (m, 1H), 7.53-7.48 (m, 3H), 7.41 (dd, J=6.8, 2.5 Hz, 1H), 4.80 (br s, 2H), 3.16 (s, 3H), 2.49 (s, 3H); ESI MS m/z 375 [C$_{20}$H$_{18}$N$_6$O$_2$+H]$^+$.

EXAMPLE 103

Preparation of (5R)-2-Amino-5-(2,6diethylpyridin-4-yl)-3-methyl-5-(3-pyrimidin-5-ylphenyl))-3,5-dihydro-4H-imidazol-4-one [A] and (5S)-2-Amino-5-(2,6diethylpyridin-4-yl)-3-methyl-5-(3-pyrimidin-5-ylphenyl))-3,5-dihydro-4H-imidazol-4-one [B]

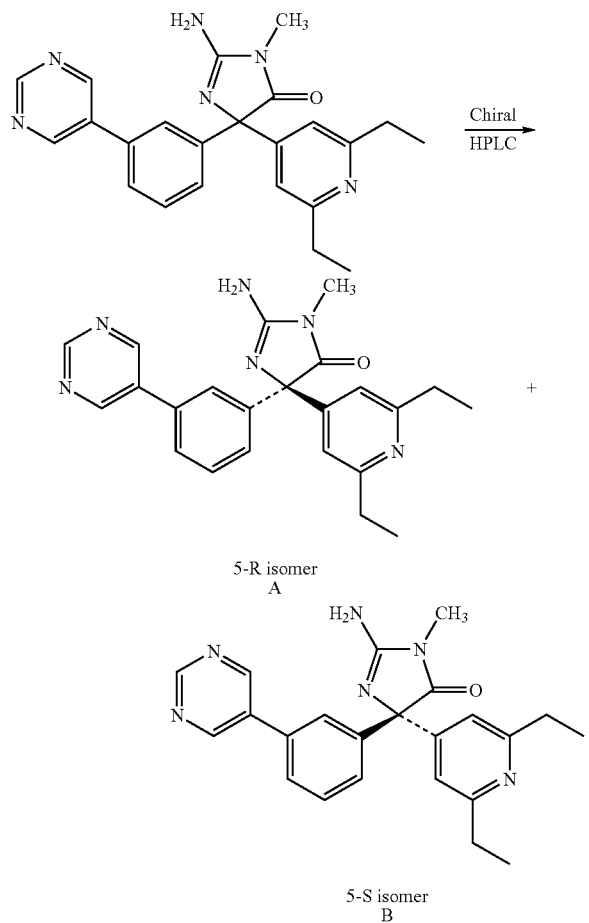

A racemic mixture of 2-amino-5-(2,6diethylpyridin-4-yl)-3-methyl-5-(3-pyrimidin-5-ylphenyl))-3,5-dihydro-4H-imidazol-4-one was separated by chiral HPLC to give the title enantiomeric products:

A: (5R)-2-Amino-5-(2,6diethylpyridin-4-yl)-3-methyl-5-(3-pyrimidin-5-ylphenyl))-3,5-dihydro-4H-imidazol-4-one, $^1$H NMR (DMSOd$_6$ 300 MHz) δ 1.15 (t, 6H), 2.63 (q, 4H), 2.95 (s, 3H), 6.72 (brs, 2H), 7.15 (s, 2H), 7.45(t, 1H), 7.5 (d 1H), 7.62 (d, 1H), 7.75 (m 1H), 8.95 (s, 2H), 9.15 (s, 1H); MS m/e (M+OH)$^+$ 401; [α]$_D^{25}$+0.039 (c=1% in CH$_3$OH); and B: (5S)-2-Amino-5-(2,6diethylpyridin-4-yl)-3-methyl-5-(3-pyrimidin-5-ylphenyl))-3,5-dihydro-4H-imidazol-4-one, $^1$H NMR (DMSOd$_6$ 300 MHz) δ 1.15 (t, 6H), 2.63 (q, 4H), 2.95 (s, 3H), 6.72 (brs, 2H), 7.15 (s, 2H), 7.45(t, 1H), 7.5 (d 1H), 7.62 (d, 1H), 7.75 (m 1H), 8.95 (s, 2H), 9.15 (s, 1H); MS m/e (M+H)$^+$ 401.

EXAMPLE 104

Preparation of 2-Amino-5-(2,6-diethyl-pyridin-4-yl)-5-[4-fluoro-3-(5-fluoropyridin-3-yl)-phenyl]-3-methyl-3,5-dihydro-imidazol-4-one

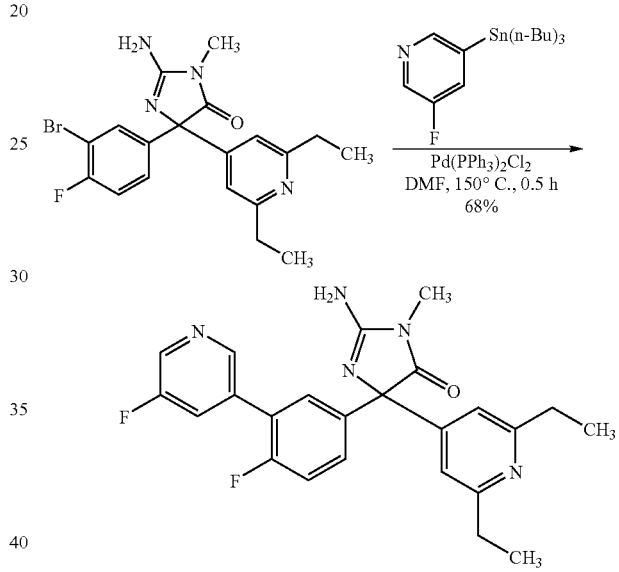

A mixture of 2-amino-5-(3-bromo-4-fluorophenyl]-5-(2,6-diethyl-pyridin-4-yl)-3-methyl-3,5-dihydro-imidazol-4-one (0.12 g, 0.286 mmol), 5-fluoropyridin-3-yl(tributyl)tin (0.166 g, 0.43 mmol) and bis(triphenylphosphino)palladium (II) chloride (0.016 g, 0.023 mmol) in DMF (5 mL) was degassed and heated at 150° C. for 0.5 h. The mixture was cooled to room temperature and diluted with ethyl acetate (50 mL) and 2% aqueous lithium chloride (20 mL). The organic layer was separated, washed with 2% aqueous lithium chloride, dried over sodium sulfate, filtered, and concentrated. Purification of the resultant residue by flash chromatography (silica, 97:3:0.25 methylene chloride/methanol/concentrated ammonium hydroxide) afforded the title product (0.085 g, 68%) as a white solid, mp 155-157° C.; $^1$H NMR (300 MHz, CD$_3$OD) 8.55 (d, J=1.5 Hz, 1H), 8.49 (d, J=2.7 Hz, 1H), 7.82 (d, J=9.6 Hz, 1H), 7.60-7.57 (m, 2H), 7.27 (dd, J=10.2, 8.7 Hz, 1H), 7.15 (s, 2H), 3.13 (s, 3H), 2.74 (q, J=7.5 Hz, 4H), 1.23 (t, J=7.5 Hz, 6H); IR (ATR) 3064, 2969, 2935, 1733, 1670, 1597, 1459, 1412, 1328, 1228, 989, 881, 783, 702 cm$^{-1}$; ESI MS m/z 436 [C$_{24}$H$_{23}$F$_2$N$_5$O+H]$^+$. Anal. Calcd for C$_{24}$H$_{23}$F$_2$N$_5$O: C, 66.19; H, 5.32; N, 16.08.

Found: C, 65.87; H, 4.73; N, 15.28.

EXAMPLE 105

Preparation of 2-Amino-5-(2,6-diethyl-pyridin-4-yl)-5-[4-fluoro-3-(4-fluoropyridin-3-yl)-phenyl]-3-methyl-3,5-dihydro-imidazol-4-one

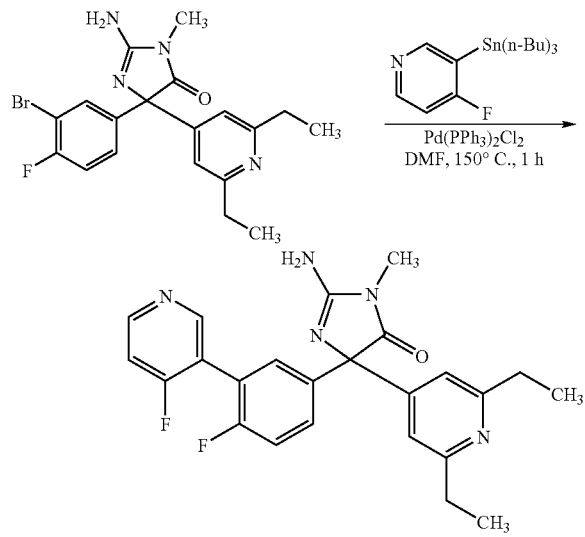

A mixture of 2-amino-5-(3-bromo-4-fluorophenyl)-5-(2,6-diethyl-pyridin-4-yl)-3-methyl-3,5-dihydro-imidazol-4-one (0.170 g, 0.405), 4-fluoropyridin-3-yl(tributyl)tin (0.235 g, 0.608 mmol) and bis(triphenylphosphino)palladium(II) chloride (0.023 g, 0.032 mmol) in DMF (5 mL) was degassed and heated at 150° C. for 1 h. The mixture was cooled to room temperature and diluted with ethyl acetate (50 mL) and 2% aqueous lithium chloride (20 mL). The organic layer was separated, washed with 2% aqueous lithium chloride, dried over sodium sulfate, filtered, and concentrated. Purification of the resultant residue by flash chromatography (silica, 95:5: 0.25 methylene chloride/methanol/concentrated ammonium hydroxide) afforded the title product (0.017 g, 10%) as a white solid, mp 92-100° C.; $^1$H NMR (300 MHz, CD$_3$OD) δ 8.55-8.45 (m, 2H), 7.56-7.19 (m, 4H), 7.09 (s, 2H), 3.10 (s, 3H), 2.68 (q, J=7.5 Hz, 4H), 1.15 (t, J=7.5 Hz, 6H); ESI MS m/z 436 [C$_{24}$H$_{23}$F$_2$N$_5$O+OH]$^+$.

EXAMPLE 106

Preparation of (5R)-2-Amino-5-(2-ethylpyridin-4-yl)-3-methyl-5-(3-pyrimidin-5-ylphenyl))-3,5-dihydro-4H-imidazol-4-one [A] and (5S)-2-Amino-5-(2-ethylpyridin-4-yl)-3-methyl-5-(3-pyrimidin-5-ylphenyl))-3,5-dihydro-4H-imidazol-4-one [B]

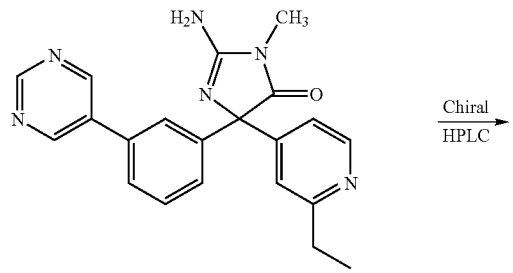

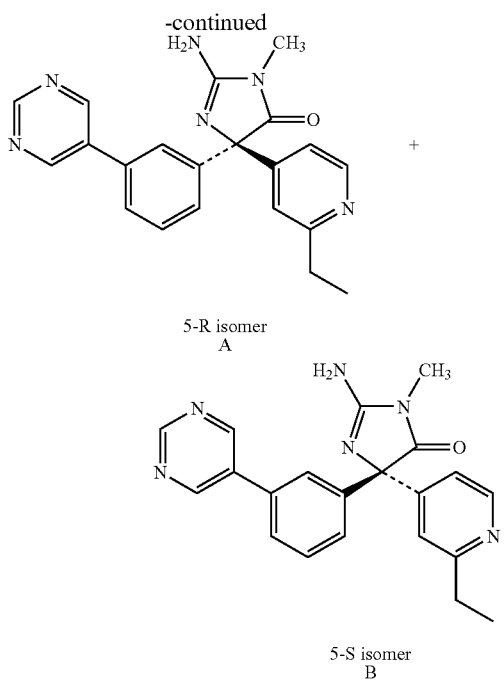

A racemic mixture of 2-amino-5-(2-ethylpyridin-4-yl)-3-methyl-5-(3-pyrimidin-5-ylphenyl))-3,5-dihydro-4H-imidazol-4-one was separated by chiral HPLC to give the title enantiomeric products:

A: (5R)-2-amino-5-(2-ethylpyridin-4-yl)-3-methyl-5-(3-pyrimidin-5-ylphenyl))-3,5-dihydro-4H-imidazol-4-one, $^1$H NMR (DMSOd$_6$ 300 MHz) δ 1.18 (t, 3H), 2.7 (t, 2H), 3.0 (s, 3H), 6.8 (brs, 2H), 7.3 2, 1H), 7.38 (s, 1H), 7.5 (t, 1H), 7.6 (d, 1H), 7.7 (d, 1H), 7.8 (s, 1H), 8.4 (d, 1H), 9.03 (s, 2H), 9.2 (s, 1H); MS m/e (M+H)$^+$ 373; and B: (5S)-2-amino-5-(2-ethylpyridin-4-yl)-3-methyl-5-(3-pyrimidin-5-ylphenyl))-3,5-dihydro-4H-imidazol-4-one, $^1$H NMR (DMSOd$_6$ 300 MHz) 61.18 (t, 3H), 2.7 (t, 2H), 3.0 (s, 3H), 6.8 (brs, 2H), 7.3 2, 1H), 7.38 (s, 1H), 7.5 (t, 1H), 7.6 (d, 1H), 7.7 (d, 1H), 7.8 (s, 1H), 8.4 (d, 1H), 9.03 (s, 2H), 9.2 (s, 1H); MS m/e (M+H)$^+$ 373; $[α]_D^{25}$=+0.031 (c=1% in CH$_3$OH)

EXAMPLE 107

Preparation of (5R)-2-Amino-5-(2,6-diethylpyridin-4-yl)-5-[(3-(2-fluoropyridin-3-yl)phenyl]-3-methyl-3,5-dihydro-4H-imidazol-4-one [A] and (5S)-2-Amino-5-(2,6-diethylpyridin-4-yl)-5-[(3-(2-fluoropyridin-3-yl)phenyl]-3-methyl-3,5-dihydro-4H-imidazol-4-one [B]

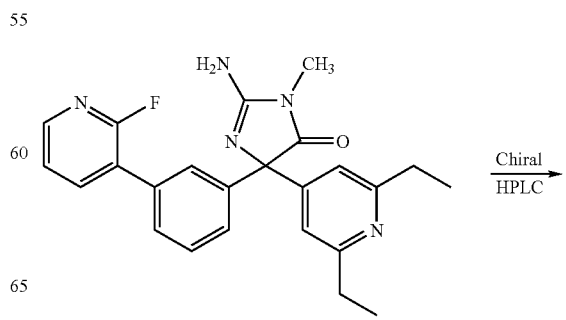

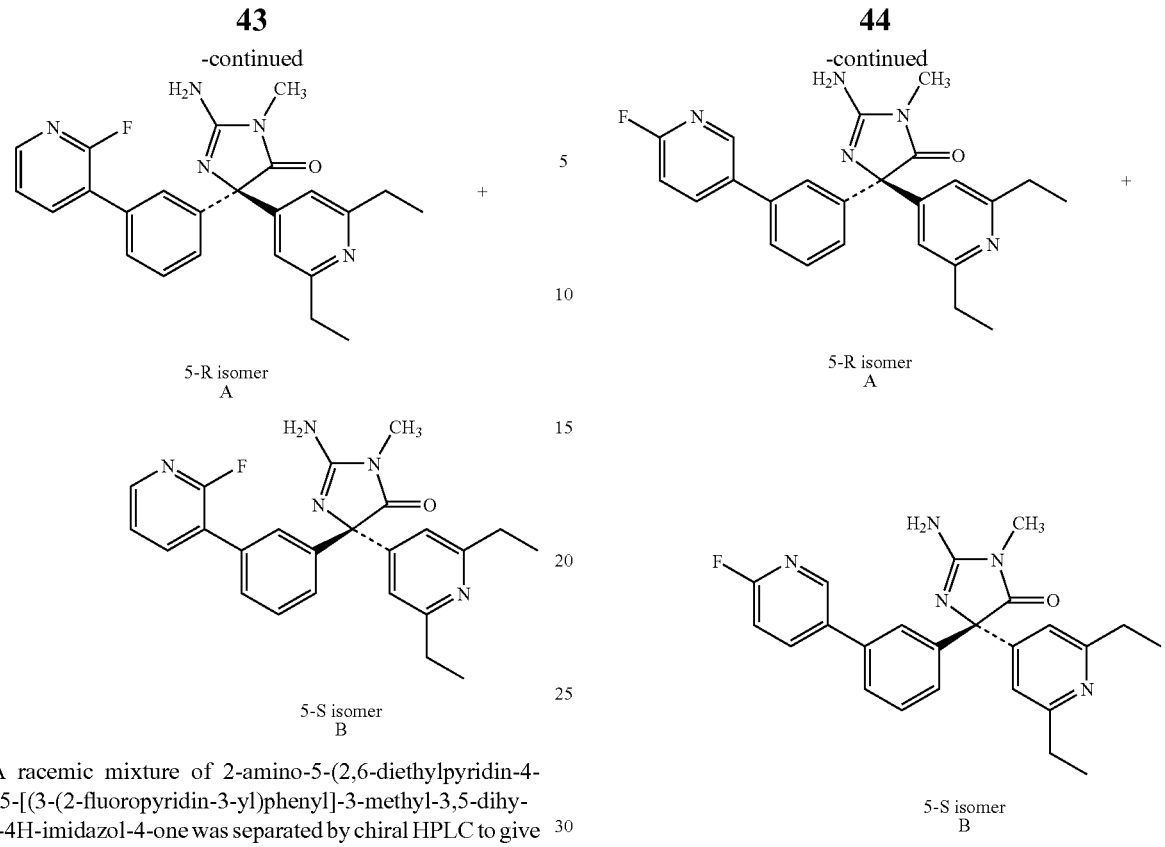

A racemic mixture of 2-amino-5-(2,6-diethylpyridin-4-yl)-5-[(3-(2-fluoropyridin-3-yl)phenyl]-3-methyl-3,5-dihydro-4H-imidazol-4-one was separated by chiral HPLC to give the title enantiomeric products:

A: (5R)-2-amino-5-(2,6-diethylpyridin-4-yl)-5-[(3-(2-fluoropyridin-3-yl)phenyl]-3-methyl-3,5-dihydro-4H-imidazol-4-one, $^1$H NMR (DMSOd$_6$ 300 MHz) δ 1.2 (t, 6H), 2.6 (q, 4H), 2.95 (s, 3H), 6.72 (brs, 2H), 7.1 (s, 1H), 7.35-7.45 (m, 3H), 7.5 (m, 1H), 7.7 (m, 1H), 8.0 (m, 2H), 8.4 (dd, 1H); MS m/e (M+H)$^+$ 418; $[α]_D^{25}$=+0.041 (c=1% in CH$_3$OH); and B: (5S)-2-amino-5-(2,6-diethylpyridin-4-yl)-5-[(3-(2-fluoropyridin-3-yl)phenyl]-3-methyl-3,5-dihydro-4H-imidazol-4-one, $^1$H NMR (DMSOd$_6$ 300 MHz) δ 1.2 (t, 6H), 2.6 (q, 4H), 2.95 (s, 3H), 6.72 (brs, 2H), 7.1 (s, 1H), 7.35-7.45 (m, 3H), 7.5 (m, 1H), 7.7 (m, 1H), 8.0 (m, 2H), 8.4 (dd, 1H); MS m/e (M+H)$^+$ 418; $[α]_D^{25}$=−0.02 (c=1% in CH$_3$OH).

EXAMPLE 108

Preparation of (5R)-2-Amino-5-(2,6-diethylpyridin-4-yl)-5-[3-(6-fluoropyridin-3-yl)phenyl]-3-methyl-3,5-dihydro-4H-imidazol-4-one [A] and (5S)-2-Amino-5-(2,6-diethylpyridin-4-yl)-5-[3-(6-fluoropyridin-3-yl)phenyl]-3-methyl-3,5-dihydro-4H-imidazol-4-one [B]

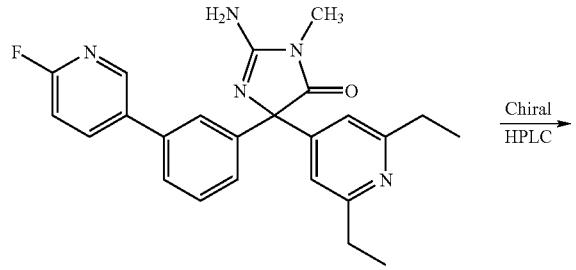

A racemic mixture of 2-amino-5-(2,6-diethylpyridin-4-yl)-5-[3-(6-fluoropyridin-3-yl)phenyl]-3-methyl-3,5-dihydro-4H-imidazol-4-one was separated by chiral HPLC to give the title enantiomeric products:

A: (5R)-2-Amino-5-(2,6-diethylpyridin-4-yl)-5-[3-(6-fluoropyridin-3-yl)phenyl]-3-methyl-3,5-dihydro-4H-imidazol-4-one, $^1$H NMR (DMSOd$_6$ 300 MHz) δ 1.15 (t, 6H), 2.6 (q, 4H), 2.95 (s, 3H), 6.72 (brs, 2H), 7.15 (s, 1H), 7.25 (dd, 1H), 7.4 (t, 1H), 7.48 (d 1H), 7.55 (d, 1H), 7.7 (m, 1H), 8.12 (m, 2H), 8.38 (m, 1H); MS m/e (M+H)$^+$ 418; $[α]_D^{25}$=+0.008 (c=1% in CH$_3$OH); and B: (5S)-2-Amino-5-(2,6-diethylpyridin-4-yl)-5-[3-(6-fluoropyridin-3-yl)phenyl]-3-methyl-3,5-dihydro-4H-imidazol-4-one, $^1$H NMR (DMSOd$_6$ 300 MHz) δ 1.15 (t, 6H), 2.6 (q, 4H), 2.95 (s, 3H), 6.72 (brs, 2H), 7.15 (s, 1H), 7.25 (dd, 1H), 7.4 (t, 1H), 7.48 (d 1H), 7.55 (d, 1H), 7.7 (m, 1H), 8.12 (m, 2H), 8.38 (m, 1H); MS m/e (M+OH)$^+$ 418; $[α]_D^{25}$=−0.002 (c=1% in CH$_3$OH).

EXAMPLE 109

Preparation of 2-Amino-5-(4-methoxy-3-methyl phenyl)-3-methyl-5-(2-phenylpyridin-4-yl)-3,5-dihydro-4H-imidazol-4-one

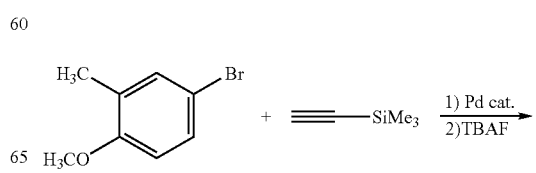

-continued

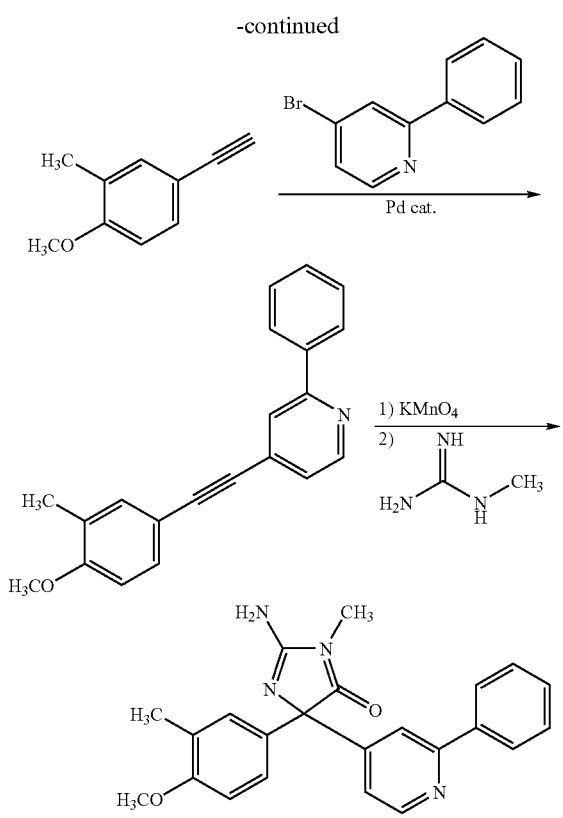

Step a) [(4-Methoxy-3-methylphenyl)ethynyl](trimethyl)silane

A solution of 4-bromo-1-methoxy-2-methylbenzene (6.702 g) in toluene was treated with tetrakis(triphenylphosphie)palladium (0) (1.15 g), followed by diisopropylamine (23 mL), trimethylsilyl acetylene (4.7 mL) and copper iodide (I) (0.127 g). The reaction was heated at 45° C. in nitrogen atmosphere overnight and evaporated to dryness. The resultant residue was applied on a large silica pad and eluted with hexane:ethyl acetate (2:1). The elute was evaporated to dryness to give the silane intermediate as a brown oil (7.167 g). The compound was characterized by LCMS analysis. LCMS Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% NH$_4$OH in water; Solvent B 0.02% NH$_4$OH in ACN; Gradient: Time O: 10% B; 2.5 min 90% B; 3 min 90% B; Sample concentration: ~2.0 mM; Injection volume: 5 uL; Detection: 220 nm, 254 nm DAD

Step b) 4-Ethynyl-1-methoxy-2-methylbenzene

A solution of [(4-methoxy-3-methylphenyl)ethynyl](trimethyl)silane (7.167 g) tetrahydrofuran was treated with TBAF (30 mL, 1.0 M solution in tetrahydrofuran), stirred for 1 hour and evaporated to dryness. The residue was dissolved in diethyl ether, washed with water, dried over anhydrous magnesium sulfate and evaporated. This residue was applied on a pad of silica and eluted with hexane:ethyl acetate (4:1). The elute was evaporated to dryness to give the alkyne intermediate as a brown solid (4.77 g). The compound was characterized by LCMS analysis. LCMS Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% NH$_4$OH in water; Solvent B 0.02% NH$_4$OH in ACN; Gradient: Time O: 10% B; 2.5 min 90% B; 3 min 90% B; Sample concentration: ~2.0 mM; Injection volume: 5 uL; Detection: 220 nm, 254 nm DAD

Step c) 4-[(4-Methoxy-3-methylphenyl)ethynyl]-2-phenylpyridine

A solution of 4-bromo-2-phenylpyridine (0.4 g; prepared according to a literature procedure: Wolf, C.; Ghebremariam, B. Synthesis 2002, 749) in toluene is treated with tetrakis(triphenylphosphine)palladium (0) (0.059 g), followed by diisopropylamine (5 mL), 4-ethynyl-1-methoxy-2-methylbenzene (1.25 g) and copper iodide (I) (0.006 g). The reaction is heated at 65° C. in nitrogen atmosphere overnight and concentrated in vacuo to give the phenylethynlypyridine intermediate as a brown oil (2.0 g). The compound was characterized by LCMS analysis. LCMS Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% NH$_4$OH in water; Solvent B 0.02% NH$_4$OH in ACN; Gradient: Time O: 10% B; 2.5 min 90% B; 3 min 90% B; Sample concentration: ~2.0 mM; Injection volume: 5 uL; Detection: 220 nm, 254 nm DAD

Step d) 1-(4-Methoxy-3-methylphenyl)-2-(2-phenylpyridin-4-yl)ethane-1,2-dione A solution of 4-[(4-methoxy-3-methylphenyl)-2-phenylpyridine (2.0 g) in acetone is treated with a solution of magnesium sulfate (0.52 g) and sodium bicarbonate (0.177 g) in water, followed by potassium permanganate (0.780 g), stirred for 2 hours and filtered through a cellite pad. The filter cake was washed with acetone. The filtrates were combined and evaporated. The resultant residue was dissolved in diethyl ether, washed sequentially with water and saturated sodium bicarbonate, dried over magnesium sulfate and concentrated in vacuo to give an oil. The oil was purified by flash chromatography hexane:ethyl acetate (9:1) to give the diketone intermediate as a bright yellow oil (0.322 g), characterized by LCMS analysis. LCMS Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% NH$_4$OH in water; Solvent B 0.02% NH$_4$OH in ACN; Gradient: Time O: 10% B; 2.5 min 90% B; 3 min 90% B; Sample concentration: ~2.0 mM; Injection volume: 5 uL; Detection: 220 nm, 254 nm DAD

Step e) 2-Amino-5-(4-methoxy-3-methylphenyl)-3-methyl-5-(2-phenylpyridin-4-yl)-3,5-dihydro-4H-imidazol-4-one A mixture of 1-(4-methoxy-3-methylphenyl)-2-(2-phenylpyridin-4-yl)ethane-1,2-dione (0.331 g, 0.5 mmol) and 1-methylguanidine hydrochloride (0.110 g, 1.0 mmol) in ethanol was treated with sodium carbonate (0.318 g, 1.5 mmol) in water (2 mL), heated at 70° C. overnight and filtered. The filtrate was evaporated to dryness to provide a residue, which was purified by Gilson preparative reverse phase HPLC system. HPLC Conditions: YMC Pro C18, 20 mm×50 mm ID, 5 uM column; 2 mL injection; Solvent A: 0.02% NH$_4$OH/water; Solvent B: 0.02% NH$_4$OH/acetonitrile; Gradient: Time O: 95% A; 2 min: 95% A; 14 min: 10% A, 15 min: 10% A, 16 min: 95% A; Flow rate 22.5 mL/min; Detection: 254 nm DAD. Compound 7 (0.110 g) to give the title product as a white, amphorous solid, characterized by LCMS analysis. LCMS Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% NH$_4$OH in water; Solvent B 0.02% NH$_4$OH in ACN; Gradient: Time O: 10% B; 2.5 min 90% B; 3 min 90% B; Sample concentration: ~2.0 mM; Injection volume: 5 uL; Detection: 220 nm, 254 nm DAD, (retention time: 2.41 min, [M−H] 385, [M+H] 387).

EXAMPLE 110

Preparation of 1-(difluoromethoxy)-4-ethynylbenzene

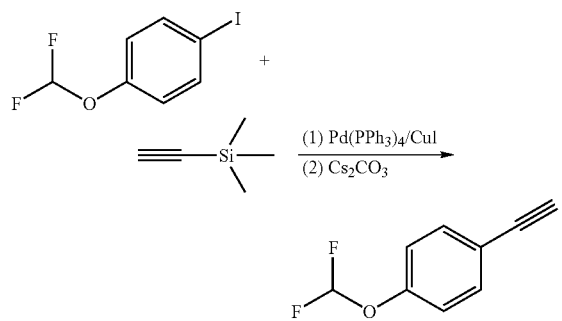

A solution of 1-(difluoromethoxy)-4-iodobenzene (12.7 g, 50 mmol) in triethylamine is treated with tetrakis(triphenylphosphine)palladium (4.0 g, 3.5 mmol), copper iodide (925 mg, 4.85 mmol), and a solution of ethynyl(trimethyl)silane (6.9 mL, 50 mmol) in acetonitrile at room temperature, stirred for 1 h at 60° C. and concentrated in vacuo. The resultant residue was dissolved in Et$_2$O and filtered. The filtrate was concentrated and the concentrate was purified by chromatography (silica gel, EtOAc/hexane: 5/95) to give {[4-(difluoromethoxy)phenyl]ethynyl}(trimethyl)silane (11.5 g, 96%) as an oil.

A solution of {[4-(difluoromethoxy)phenyl]ethynyl}(trimethyl)silane (10.0 g, 41.7 mmol) in MeOH/CH$_2$Cl$_2$ (1/1) was treated with cesium carbonate (16.3 g, 50 mmol) at room temperature, stirred for 1.5 h, diluted with CH$_2$Cl$_2$ and filtered through a pad of silica gel. The filtrate was concentrated to dryness to give the title compound (6.8 g, 97%) as an oil. MS (+) EI: 168.

EXAMPLE 111

Preparation of 2-amino-5-[4-(difluoromethoxy)phenyl]-3-methyl-5-pyridin-3-yl-3,5-dihydro-4H-imidazol-4-one

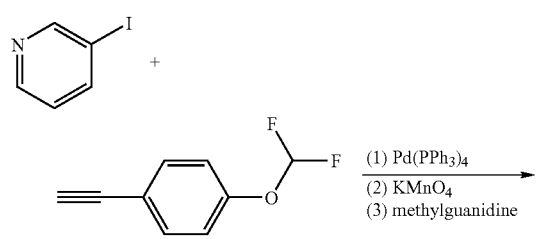

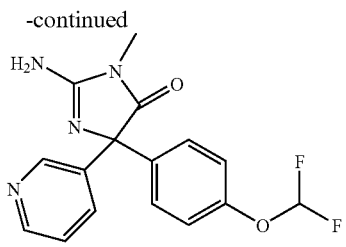

A solution of 3-iodopyridine (205 mg, 1.0 mg) in triethylamine was treated with tetrakis(triphenylphosphine)palladium (80 mg, 0.069 mmol), copper iodide (18 mg, 0.097 mmol) and a solution of 1-(difluoromethoxy)-4-ethynylbenzene (168 mg, 1.0 mmol) in acetonitrile at room temperature, heated at 60° C. for 1 h, cooled and concentrated to dryness to afford 3-{[4-(difluoromethoxy)phenyl]ethynyl}pyridine as a residue. The residue (240 mg) was dissolved in acetone, treated sequentially with a solution of NaHCO$_3$ (50 mg) and MgSO$_4$ (180 mg) in H$_2$O and KMnO$_4$ (327 mg), stirred for 10 minutes at room temperature and extracted with 1/1 Et$_2$O/hexane. The combined extracts were concentrated to dryness to give 1-[4-(difluoromethoxy)phenyl]-2-pyridin-3-ylethane-1,2-dione. A mixture of 1-[4-(difluoromethoxy)phenyl]-2-pyridin-3-ylethane-1,2-dione (230 mg), N-methylguanidine hydrochloride (155 mg) and Na$_2$CO$_3$ (240 mg) in ethanol was heated at reflux temperature for 1.5 h. and concentrated in vacuo. The resultant residue was purified by chromatography (silica gel, EtOAc/2.0 M NH$_3$ in EtOH: 97/3) to give the title compound (130 mg) as a solid, mp: 173-175° C., identified by NMR and mass spectral analyses. MS (+) APPI: 333 (M+H)$^+$.

EXAMPLE 112

Preparation of 2-amino-5-[4-(difluoromethoxy)phenyl]-3-methyl-5-pyridin-4-yl-3,5-dihydro-4H-imidazol-4-one

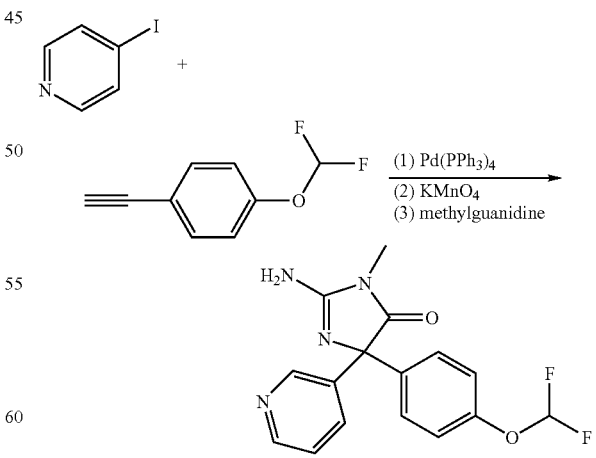

Using essentially the same procedure described in Example 111 and employing 4-iodopyridine, the title compound was obtained as a solid, mp: 193-195° C., identified by NMR and mass spectral analyses. MS (+) APPI: 333 (M+H)$^+$.

EXAMPLE 113

Preparation of (5R)-2-amino-5-[4-fluoro-3-(2-fluoropyridin-3-yl)phenyl]-3-methyl-5-pyridin-4-yl-3,5-dihydro-4H-imidazol-4-one [A] and (5S)-2-amino-5-[4-fluoro-3-(2-fluoropyridin-3-yl)phenyl]-3-methyl-5-pyridin-4-yl-3,5-dihydro-4H-imidazol-4-one [B]

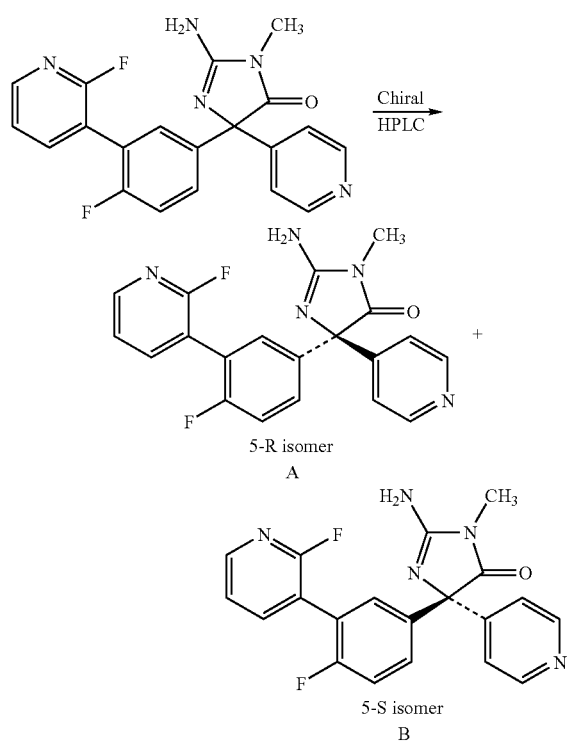

A racemic mixture of 2-amino-5-[4-fluoro-3-(2-fluoropyridin-3-yl)phenyl]-3-methyl-5-pyridin-4-yl-3,5-dihydro-4H-imidazol-4-one was separated by chiral HPLC to give the title enantiomeric products:

A: (5R)-2-amino-5-[4-fluoro-3-(2-fluoropyridin-3-yl)phenyl]-3-methyl-5-pyridin-4-yl-3,5-dihydro-4H-imidazol-4-one, MS m/e (M+H)$^+$ 380; $[\alpha]_D^{25}$=+13.6 (c=1% in DMSO); and B: (5S)-2-amino-5-[4-fluoro-3-(2-fluoropyridin-3-yl)phenyl]-3-methyl-5-pyridin-4-yl-3,5-dihydro-4H-imidazol-4-one, MS m/e (M+H)$^+$ 380; $[\alpha]_D^{25}$=−13.6 (c=1% in DMSO).

EXAMPLE 114

Evaluation of BACE-1 Binding Affinity of Test Compounds

Fluorescent Kinetic Assays

Final Assay Conditions: 10 nM human BACE1 (or 10 nM Murine BACE1, 1.5 nM human BACE2), 25 μM substrate (WABC-6, MW 1549.6, from AnaSpec), Buffer: 50 mM Na-Acetate, pH 4.5, 0.05% CHAPS, 25% PBS, room temperature. Na-Acetate was from Aldrich, Cat.# 24,124-5, CHAPS was from Research Organics, Cat. # 1304C$_1$×, PBS was from Mediatech (Celigro), Cat# 21-031-CV, peptide substrate AbzSEVNLDAEFRDpa was from AnaSpec, Peptide Name: WABC-6

Determination of stock substrate (AbzSEVNLDAEFRDpa) concentration: ~25 mM stock solution is made in DMSO using the peptide weight and MW, and diluted to ~25 μM (1:1000) in 1×PBS. Concentration is determined by absorbance at 354 nm using an extinction coefficient ϵ of 18172 M$^{-1}$ cm$^{-1}$, the concentration of stock substrate is corrected, and the substrate stock stored in small aliquots in −80° C. [Substrate Stock]=ABS$^{354\ nm}$*10$^6$/18172 (in mM)

The extinction coefficient 354 nm was adapted from TACE peptide substrate, which had the same quencher-fluorophore pair.

Determination of Stock Enzyme Concentration: the stock concentration of each enzyme is determined by absorbance at 280 nm using an ϵ of 64150 M$^{-1}$ cm$^{-1}$ for hBACE1 and MuBACE1, 62870 M$^{-1}$ cm$^{-1}$ for hBACE2 in 6 M Guanidinium Hydrochloride (from Research Organics, Cat. # 5134G-2), pH ~6. The extinction coefficient $\epsilon^{280\ nm}$ for each enzyme was calculated based on known amino acid composition and published extinction coefficients for Trp (5.69 M$^{-1}$ cm$^{-1}$) and Tyr (1.28 M$^{-1}$ cm$^{-1}$) residues (*Anal. Biochem.* 182, 319-326).

Dilution and mixing steps: total reaction volume: 100 μL
2× inhibitor dilutions in buffer A (66.7 mM Na-Acetate, pH 4.5, 0.0667% CHAPS) were prepared,
4× enzyme dilution in buffer A (66.7 mM Na-Acetate, pH 4.5, 0.0667% CHAPS) were prepared,
100 μM substrate dilution in 1×PBS was prepared, and
50 μL 2× Inhibitor, 25 μL 100 μM substrate are added to each well of 96-well plate (from DYNEX Technologies, VWR #: 11311-046), immediately followed by 25 μL 4× enzyme (added to the inhibitor and substrate mix), and the fluorescence readings are initiated.

Fluorescence Readings: Readings at $\lambda_{ex}$ 320 nm and $\epsilon_{em}$ 420 nm are taken every 40 sec for 30 min at room temperature and the linear slope for substrate cleavage rate ($v_i$) determined.

Calculation of % Inhibition:

$$\% \text{ Inhibition}=100*(1-v_i/v_0)$$

$v_i$: substrate cleavage rate in the presence of inhibitor $v_0$: substrate cleavage rate in the absence of inhibitor IC$_{50}$ Determination:

$$\% \text{ Inhibition}=((B*IC_{50}{}^n)+(100*I_0{}^n))/(IC_{50}{}^n+I_0{}^n)$$

(Model # 39 from LSW Tool Bar in Excel where B is the % inhibition from the enzyme control, which should be close to 0.) % Inhibition is plotted vs. Inhibitor Concentration (I$_0$) and the data fit to the above equation to obtain IC$_{50}$ value and Hill number (n) for each compound. Testing at least 10 different inhibitor concentrations is preferred. The data obtained are shown in Table IX, hereinbelow.

TABLE IX

| Ex No. | BACE-1 (IC$_{50}$ μM) |
|---|---|
| 23 | C |
| 24 | C |
| 25 | C |
| 26 | B |

TABLE IX-continued

| Ex No. | BACE-1 (IC$_{50}$ µM) |
|---|---|
| 27 | B |
| 28 | C |
| 29 | B |
| 30 | A |
| 31 | A |
| 32 | B |
| 33 | A |
| 34 | A |
| 35 | B |
| 36 | B |
| 37 | B |
| 38 | B |
| 39 | A |
| 40 | A |
| 41 | A |
| 42 | B |
| 43 | A |
| 44 | A |
| 45 | B |
| 46 | B |
| 47 | C |
| 48 | B |
| 49 | B |
| 50 | B |
| 51 | C |
| 52 | — |
| 53 | A |
| 54 | B |
| 55 | A |
| 56 | A |
| 57 | B |
| 58 | A |
| 59 | A |
| 60 | A |
| 61 | A |
| 62 | A |
| 63 | A |
| 64 | A |
| 65 | — |
| 66 | A |
| 67 | A |
| 70 | A |
| 71 | B |
| 72 | B |
| 73 | A |
| 74 | B |
| 75 | B |
| 76 | B |
| 78 | — |
| 79 | — |
| 80 | — |
| 81 | — |
| 82 | — |
| 83 | B |
| 84 | B |
| 85 | B |
| 86 | B |
| 87 | A |
| 88 | B |
| 89 | A |
| 90 | A |
| 91 | A |
| 92 | B |
| 93 | B |
| 94 | — |
| 95 | — |
| 96 | A |
| 97 | C |
| 98 | B |
| 99 | B |
| 100 | A |
| 101 | B |
| 102 | B |
| 103A | C |
| 103B | A |
| 104 | A |
| 105 | — |
| 106A | C |
| 106B | A |
| 107A | C |
| 107B | A |
| 108A | C |
| 108B | A |
| 109 | B |
| 111 | C |
| 112 | C |
| 113A | C |
| 113B | C |

For Table IX
A = 0.01 µM – 0.10 µM
B = 0.11 µM – 1.00 µM
C = >1.00 µM

What is claimed is:

1. A compound of formula I

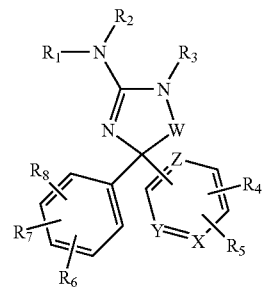

wherein W is CO, CS or CH$_2$;
X is N, NO, or CR;
Y is N, NO, or CR$_{10}$;
Z is N, NO, or CR$_{11}$ with the proviso that at least one of X, Y or Z must be N or NO;
R$_1$ and R$_2$ are each independently H, COR$_{34}$, CO$_2$R$_{12}$ or an optionally substituted C$_1$-C$_4$alkyl group;
R$_3$ is H, OR$_{13}$ or a C$_1$-C$_6$alkyl, C$_1$-C$_6$haloalkyl, C$_2$-C$_6$alkenyl, C$_2$-C$_6$alkynyl, C$_3$-C$_8$cycloalkyl or aryl (C$_1$-C$_6$)alkyl group each optionally substituted;
R$_4$ and R$_5$ are each independently H, halogen, NO$_2$, CN, OR$_{14}$, CO$_2$R$_{15}$, COR$_{16}$, NR$_{17}$R$_{18}$, SO$_p$NR$_{19}$R$_{20}$ or a C$_1$-C$_6$alkyl, C$_1$-C$_6$haloalkyl, C$_2$-C$_6$alkenyl, C$_2$-C$_6$alkynyl or C$_3$-C$_8$cycloalkyl group each optionally substituted;
R$_6$ is H, halogen, NO$_2$, CN, OR$_{21}$, NR$_{22}$R$_{23}$ or a C$_1$-C$_6$alkyl, C$_1$-C$_6$haloalkyl, C$_2$-C$_6$alkenyl, C$_2$-C$_6$alkynyl or C$_3$-C$_8$cycloalkyl group each optionally substituted;
R$_7$ is H, halogen, NO$_2$, CN, OR$_{24}$, NR$_{25}$R$_{26}$ or a C$_1$-C$_6$alkyl, C$_1$-C$_6$haloalkyl, C$_2$-C$_6$alkenyl, C$_2$-C$_6$alkynyl, C$_3$-C$_8$cycloalkyl, aryl or heteroaryl group each optionally substituted;
R, R$_8$, R$_9$ and R$_{10}$ are each independently H, halogen, NO$_2$, CN, OR$_{27}$, CO$_2$R$_{28}$, COR$_{29}$, NR$_{30}$R$_{31}$, SO$_p$NR$_{32}$R$_{33}$ or a C$_1$-C$_6$alkyl, C$_1$-C$_6$haloalkyl, C$_2$-C$_6$alkenyl, C$_2$-C$_6$alkynyl or C$_3$-C$_8$cycloalkyl group each optionally substituted;
R$_{11}$, R$_{12}$, R$_{13}$, R$_{14}$, R$_{15}$, R$_{16}$, R$_{21}$, R$_{24}$, R$_{27}$, R$_{28}$ and R$_{29}$ are each independently H or a C$_1$-C$_6$alkyl, C$_1$-C$_6$haloalkyl, $C_2$-$C_6$alkenyl, $C_2$-$C_6$alkynyl, $C_3$-$C_8$cycloalkyl, cycloheteroalkyl or aryl group each optionally substituted;

$R_{17}$, $R_{18}$, $R_{19}$, $R_{20}$, $R_{22}$, $R_{23}$, $R_{25}$, $R_{26}$, $R_{30}$, $R_{31}$, $R_{32}$ and $R_{33}$ are each independently H, $COR_{34}$, $SO_pR_{35}$ or a $C_1$-$C_4$alkyl, $C_2$-$C_6$alkenyl, $C_2$-$C_6$alkynyl, $C_3$-$C_8$ cycloalkyl, cycloheteroalkyl, aryl or heteroaryl group each optionally substituted or $R_{17}$, $R_{18}$; or $R_{19}$, $R_{20}$, or $R_{22}$, $R_{23}$, or $R_{25}$, $R_{26}$, or $R_{30}$, $R_{31}$, or $R_{32}$, $R_{33}$ may be taken together with the atom to which they are attached to form an optionally substituted 5- to 7-membered ring optionally containing an additional heteroatom selected from O, N or S;

$R_{34}$ is H, or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted; and $R_{35}$ is a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted; or a tautomer thereof, a stereoisomer thereof or a pharmaceutically acceptable salt thereof.

2. The compound according to claim 1 wherein W is CO; X is N; Y is $CR_{10}$ and Z is $CR_{11}$.

3. The compound according to claim 1 wherein W is CO and $R_7$ is phenyl or heteroaryl.

4. The compound according to claim 1 wherein W is CO; $R_1$ and $R_2$ are H; and $R_3$ is H or $C_1$-$C_3$alkyl.

5. The compound according to claim 2 wherein $R_7$ is phenyl or heteroaryl.

6. The compound according to claim 2 wherein $R_{10}$ and $R_{11}$ are H.

7. The compound according to claim 2 wherein $R_7$ is an optionally subtstituted pyridinyl group.

8. The compound according to claim 7 wherein $R_1$ and $R_2$ are H; and $R_3$ is methyl.

9. The compound according to claim 1 selected from the group consisting essentially of:

(5S)-2-amino-5-[4-fluoro-3-(2-fluoropyridin-3-yl)phenyl]-3-methyl-5-pyridin-4-yl-3,5-dihydro-4H-imidazol-4-one;

2-amino-3-methyl-5-phenyl-5-pyridin-4-yl-3,5-dihydro-4H-imidazol-4-one;

2-amino-5-(3-bromophenyl)-3-methyl-5-pyridin-4-yl-3,5-dihydro-4H-imidazol-4-one;

2-amino-5-(3-methoxyphenyl)-3-methyl-5-pyridin-4-yl-3,5-dihydro-4H-imidazol-4-one;

2-amino-5-(1,1'-biphenyl-3-yl)-3-methyl-5-pyridin-4-yl-3,5-dihydro-4H-imidazol-4-one;

2-amino-5-(1,1'-biphenyl-3-yl)-3-methyl-5-pyridin-3-yl-3,5-dihydro-4H-imidazol-4-one;

2-amino-3-methyl-5-phenyl-5-pyridin-3-yl-3,5-dihydro-4H-imidazol-4-one;

2-amino-5-(3-hydroxyphenyl)-3-methyl-5-pyridin-4-yl-3,5-dihydro-4H-imidazol-4-one;

2-amino-5-(3'-fluoro-1,1'-biphenyl-3-yl)-3-methyl-5-pyridin-4-yl-3,5-dihydro-4H-imidazol-4-one;

2-amino-5-(3',5'-difluoro-1,1'-biphenyl-3-yl)-3-methyl-5-pyridin-4-yl-3,5-dihydro-4H-imidazol-4-one;

2-amino-5-(2',5'-difluoro-1,1'-biphenyl-3-yl)-3-methyl-5-pyridin-4-yl-3,5-dihydro-4H-imidazol-4-one;

2-amino-3-methyl-5-pyridin-4-yl-5-[3'-(trifluoromethyl)-1,1'-biphenyl-3-yl]-3,5-dihydro-4H-imidazol-4-one;

2-amino-3-methyl-5-pyridin-4-yl-5-[3'-(trifluoromethoxy)-1,1'-biphenyl-3-yl]-3,5-dihydro-4H-imidazol-4-one;

3'-(2-amino-1-methyl-5-oxo-4-pyridin-4-yl-4,5-dihydro-1H-imidazol-4-yl)-1,1'-biphenyl-3-carbonitrile;

2-amino-3-methyl-5-(3-pyrazin-2-ylphenyl)-5-pyridin-4-yl-3,5-dihydro-4H-imidazol-4-one;

2-amino-5-(3'-methoxy-1,1'-biphenyl-3-yl)-3-methyl-5-pyridin-4-yl-3,5-dihydro-4H-imidazol-4-one;

2-amino-5-(3'-hydroxy-1,1'-biphenyl-3-yl)-3-methyl-5-pyridin-4-yl-3,5-dihydro-4H-imidazol-4-one;

2-amino-5-(1,1'-biphenyl-3-yl)-3-methyl-5-(2-methylpyridin-4-yl)-3,5-dihydro-4H-imidazol-4-one;

2-amino-5-(2',5'-difluoro-1,1'-biphenyl-3-yl)-3-methyl-5-(2-methylpyridin-4-yl)-3,5-dihydro-4H-imidazol-4-one;

2-amino-5-(2',5'-difluoro-1,1'-biphenyl-3-yl)-5-(2-ethylpyridin-4-yl)-3-methyl-3,5-dihydro-4H-imidazol-4-one;

2-amino-5-(2',5'-difluoro-1,1'-biphenyl-3-yl)-3-methyl-5-(2-propylpyridin-4-yl)-3,5-dihydro-4H-imidazol-4-one;

2-amino-5-(2',5'-difluoro-1,1'-biphenyl-3-yl)-5-(2-isopropylpyridin-4-yl)-3-methyl-3,5-dihydro-4H-imidazol-4-one;

2-amino-5-(2',5'-difluoro-1,1'-biphenyl-3-yl)-5-(2-fluoropyridin-4-yl)-3-methyl-3,5-dihydro-4H-imidazol-4-one;

2-amino-5-(2',5'-difluoro-1,1'-biphenyl-3-yl)-5-(3-fluoropyridin-4-yl)-3-methyl-3,5-dihydro-4H-imidazol-4-one;

2-amino-3-methyl-5-pyridin-4-yl-5-(3-thien-2-ylphenyl)-3,5-dihydro-4H-imidazol-4-one;

2-amino-3-methyl-5-pyridin-4-yl-5-(3-thien-3-ylphenyl)-3,5-dihydro-4H-imidazol-4-one;

2-amino-5-[3-(2-furyl)phenyl]-3-methyl-5-pyridin-4-yl-3,5-dihydro-4H-imidazol-4-one;

2-amino-5-[3-(3-furyl)phenyl]-3-methyl-5-pyridin-4-yl-3,5-dihydro-4H-imidazol-4-one;

2-amino-3-methyl-5-(3-propoxyphenyl)-5-pyridin-4-yl-3,5-dihydro-4H-imidazol-4-one;

2-amino-5-(3-isobutoxyphenyl)-3-methyl-5-pyridin-4-yl-3,5-dihydro-4H-imidazol-4-one;

2-amino-5-[3-(but-3-ynyloxy)phenyl]-3-methyl-5-pyridin-4-yl-3,5-dihydro-4H-imidazol-4-one;

N-[3-(2-amino-1-methyl-5-oxo-4-pyridin-4-yl-4,5-dihydro-1H-imidazol-4-yl)phenyl]-2-methoxyacetamide;

N-[3-(2-amino-1-methyl-5-oxo-4-pyridin-4-yl-4,5-dihydro-1H-imidazol-4-yl)phenyl]-2-furamide;

3-(2-amino-1-methyl-5-oxo-4-pyridin-4-yl-4,5-dihydro-1H-imidazol-4-yl)-N-propylbenzamide;

2-amino-5-(3-bromophenyl)-3-methyl-5-(2-methylpyridin-4-yl)-3,5-dihydro-4H-imidazol-4-one;

2-amino-3-methyl-5-(2-methylpyridin-4-yl)-5-(3-pyridin-3-ylphenyl)-3,5-dihydro-4H-imidazol-4-one;

2-amino-3-methyl-5-(2-methylpyridin-4-yl)-5-(3-pyrimidin-5-ylphenyl)-3,5-dihydro-4H-imidazol-4-one;

2-amino-5-(2',5'-difluoro-1,1'-biphenyl-3-yl)-3-methyl-5-(2-methylpyridin-4-yl)-3,5-dihydro-4H-imidazol-4-one;

2-amino-5-(2-ethylpyridin-4-yl)-3-methyl-5-(3-pyridin-3-ylphenyl)-3,5-dihydro-4H-imidazol-4-one;

2-amino-5-(2-ethylpyridin-4-yl)-3-methyl-5-(3-pyrimidin-5-ylphenyl)-3,5-dihydro-4H-imidazol-4-one;

2-amino-5-(2',5'-difluoro-1,1'-biphenyl-3-yl)-5-(2-ethylpyridin-4-yl)-3-methyl-3,5-dihydro-4H-imidazol-4-one;

2-amino-3-methyl-5-(2-methylpyridin-4-yl)-5-(3-pyrazin-2-ylphenyl)-3,5-dihydro-4H-imidazol-4-one;

2-amino-5-(2-ethylpyridin-4-yl)-3-methyl-5-(3-pyrazin-2-ylphenyl)-3,5-dihydro-4H-imidazol-4-one;

2-amino-5-(2,6-dimethylpyridin-4-yl)-3-methyl-5-(3-pyridin-3-ylphenyl)-3,5-dihydro-4H-imidazol-4-one;
2-amino-5-(2,6-dimethylpyridin-4-yl)-3-methyl-5-(3-pyrimidin-5-ylphenyl)-3,5-dihydro-4H-imidazol-4-one;
2-amino-5-(2',5'-difluoro-1,1'-biphenyl-3-yl)-5-(2,6-dimethylpyridin-4-yl)-3-methyl-3,5-dihydro-4H-imidazol-4-one;
2-amino-5-(2,6-dimethylpyridin-4-yl)-3-methyl-5-(3-pyrazin-2-ylphenyl)-3,5-dihydro-4H-imidazol-4-one;
2-amino-5-(2,6-diethylpyridin-4-yl)-3-methyl-5-(3-pyridin-3-ylphenyl)-3,5-dihydro-4H-imidazol-4-one;
2-amino-3-methyl-5-pyridin-4-yl-5-(3-pyridin-3-ylphenyl)-3,5-dihydro-4H-imidazol-4-one;
a tautomer thereof;
a stereoisomer thereof; and
a pharmaceutically acceptable salt thereof.

10. A pharmaceutical composition which comprises a pharmaceutically acceptable carrier and an effective amount of a compound of formula I

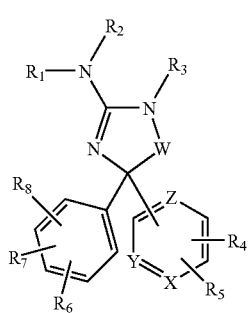

wherein W is CO, CS or $CH_2$;
X is N, NO, or CR;
Y is N, NO, or $CR_{10}$;
Z is N, NO, or $CR_{11}$ with the proviso that at least one of X, Y or Z must be N or NO;
$R_1$ and $R_2$ are each independently H, $COR_{34}$, $CO_2R_{12}$ or an optionally substituted $C_1$-$C_4$alkyl group;
$R_3$ is H, $OR_{13}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or aryl$(C_1$-$C_6)$alkyl group each optionally substituted;
$R_4$ and $R_5$ are each independently H, halogen, $NO_2$, CN, $OR_{14}$, $CO_2R_{15}$, $COR_{16}$, $NR_{17}R_{18}$, $SO_pNR_{19}R_{20}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
$R_6$ is H, halogen, $NO_2$, CN, $OR_{21}$, $NR_{22}R_{23}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
$R_7$ is H, halogen, $NO_2$, CN, $OR_{24}$, $NR_{25}R_{26}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, aryl or heteroaryl group each optionally substituted;
R, $R_8$, $R_9$ and $R_{10}$ are each independently H, halogen, $NO_2$, CN, $OR_{27}$, $CO_2R_{28}$, $COR_{29}$, $NR_3OR_{31}$, $SO_pNR_{32}R_{33}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
$R_{11}$, $R_{12}$, $R_{13}$, $R_{14}$, $R_{15}$, $R_{16}$, $R_{21}$, $R_{24}$, $R_{27}$, $R_{28}$ and $R_{29}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl or aryl group each optionally substituted;

$R_{17}$, $R_{18}$, $R_{19}$, $R_{20}$, $R_{22}$, $R_{23}$, $R_{25}$, $R_{26}$, $R_{30}$, $R_{31}$, $R_{32}$ and $R_{33}$ are each independently H, $COR_{34}$, $SO_pR_{35}$ or a $C_1$-$C_4$alkyl, $C_2$-$C_6$alkenyl, $C_2$-$C_6$alkynyl, $C_3$-$C_8$cycloalkyl, cycloheteroalkyl, aryl or heteroaryl group each optionally substituted or $R_{17}$, $R_{18}$; or $R_{19}$, $R_{20}$, or $R_{22}$, $R_{23}$, or $R_{25}$, $R_{26}$, or $R_{30}$, $R_{31}$, or $R_{32}$, $R_{33}$ may be taken together with the atom to which they are attached to form an optionally substituted 5- to 7-membered ring optionally containing an additional heteroatom selected from O, N or S;
$R_{34}$ is H, or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted; and
$R_{35}$ is a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted; or
a tautomer thereof, a stereoisomer thereof or a pharmaceutically acceptable salt thereof.

11. The composition according to claim 10 having a formula I compound wherein W is O; X is N; Y is $CR_{10}$ and Z is $CR_{11}$.

12. The composition according to claim 11 having a formula I compound wherein $R_7$ is phenyl or heteroaryl.

13. The composition according to claim 12 having a formula I compound wherein $R_1$ and $R_2$ are H and $R_3$ is H or $C_1$-$C_3$alkyl.

14. The composition according to claim 13 having a formula I compound wherein $R_7$ is an optionally substituted pyridinyl group and $R_{10}$ and $R_{11}$, are H.

15. The composition according to claim 10 having a formula I compound selected from the group consisting essentially of:
(5S)-2-amino-5-[4-fluoro-3-(2-fluoropyridin-3-yl)phenyl]-3-methyl-5-pyridin-4-yl-3,5-dihydro-4H-imidazol-4-one;
2-amino-3-methyl-5-phenyl-5-pyridin-4-yl-3,5-dihydro-4H-imidazol-4-one;
2-amino-5-(3-bromophenyl)-3-methyl-5-pyridin-4-yl-3,5-dihydro-4H-imidazol-4-one;
2-amino-5-(3-methoxyphenyl)-3-methyl-5-pyridin-4-yl-3,5-dihydro-4H-imidazol-4-one;
2-amino-5-(1,1'-biphenyl-3-yl)-3-methyl-5-pyridin-4-yl-3,5-dihydro-4H-imidazol-4-one;
2-amino-5-(1,1'-biphenyl-3-yl)-3-methyl-5-pyridin-3-yl-3,5-dihydro-4H-imidazol-4-one;
2-amino-3-methyl-5-phenyl-5-pyridin-3-yl-3,5-dihydro-4H-imidazol-4-one;
2-amino-5-(3-hydroxyphenyl)-3-methyl-5-pyridin-4-yl-3,5-dihydro-4H-imidazol-4-one;
2-amino-5-(3'-fluoro-1,1'-biphenyl-3-yl)-3-methyl-5-pyridin-4-yl-3,5-dihydro-4H-imidazol-4-one;
2-amino-5-(3',5'-difluoro-1,1'-biphenyl-3-yl)-3-methyl-5-pyridin-4-yl-3,5-dihydro-4H-imidazol-4-one;
2-amino-5-(2',5'-difluoro-1,1'-biphenyl-3-yl)-3-methyl-5-pyridin-4-yl-3,5-dihydro-4H-imidazol-4-one;
2-amino-3-methyl-5-pyridin-4-yl-5-[3'-(trifluoromethyl)-1,1'-biphenyl-3-yl]-3,5-dihydro-4H-imidazol-4-one;
2-amino-3-methyl-5-pyridin-4-yl-5-[3'-(trifluoromethoxy)-1,1'-biphenyl-3-yl]-3,5-dihydro-4H-imidazol-4-one;
3'-(2-amino-1-methyl-5-oxo-pyridin-4-yl-4,5-dihydro-1H-imidazol-4-yl)-1,1'-biphenyl-3-carbonitrile;
2-amino-3-methyl-5-(3-pyrazin-2-ylphenyl)-5-pyridin-4-yl-3,5-dihydro-4H-imidazol-4-one;
2-amino-5-(3'-methoxy-1,1'-biphenyl-3-yl)-3-methyl-5-pyridin-4-yl-3,5-dihydro-4H-imidazol-4-one;

2-amino-5-(3'-hydroxy-1,1'-biphenyl-3-yl)-3-methyl-5-pyridin-4-yl-3,5-dihydro-4H-imidazol-4-one;
2-amino-5-(1,1'-biphenyl-3-yl)-3-methyl-5-(2-methylpyridin-4-yl)-3,5-dihydro-4H-imidazol-4-one;
2-amino-5-(2',5'-difluoro-1,1'-biphenyl-3-yl)-3-methyl-5-(2-methylpyridin-4-yl)-3,5-dihydro-4H-imidazol-4-one;
2-amino-5-(2',5'-difluoro-1,1'-biphenyl-3-yl)-5-(2-ethylpyridin-4-yl)-3-methyl-3,5-dihydro-4H-imidazol-4-one;
2-amino-5-(2',5'-difluoro-1,1'-biphenyl-3-yl)-3-methyl-5-(2-propylpyridin-4-yl)-3,5-dihydro-4H-imidazol-4-one;
2-amino-5-(2',5'-difluoro-1,1'-biphenyl-3-yl)-5-(2-isopropylpyridin-4-yl)-3-methyl-3,5-dihydro-4H-imidazol-4-one;
2-amino-5-(2',5'-difluoro-1,1'-biphenyl-3-yl)-5-(2-fluoropyridin-4-yl)-3-methyl-3,5-dihydro-4H-imidazol-4-one;
2-amino-5-(2',5'-difluoro-1,1'-biphenyl-3-yl)-5-(3-fluoropyridin-4-yl)-3-methyl-3,5-dihydro-4H-imidazol-4-one;
2-amino-3-methyl-5-pyridin-4-yl-5-(3-thien-2-ylphenyl)-3,5-dihydro-4H-imidazol-4-one;
2-amino-3-methyl-5-pyridin-4-yl-5-(3-thien-3-ylphenyl)-3,5-dihydro-4H-imidazol-4-one;
2-amino-5-[3-(2-furyl)phenyl]-3-methyl-5-pyridin-4-yl-3,5-dihydro-4H-imidazol-4-one;
2-amino-5-[3-(3-furyl)phenyl]-3-methyl-5-pyridin-4-yl-3,5-dihydro-4H-imidazol-4-one;
2-amino-3-methyl-5-(3-propoxyphenyl)-5-pyridin-4-yl-3,5-dihydro-4H-imidazol-4-one;
2-amino-5-(3-isobutoxyphenyl)-3-methyl-5-pyridin-4-yl-3,5-dihydro-4H-imidazol-4-one;
2-amino-5-[3-(but-3-ynyloxy)phenyl]-3-methyl-5-pyridin-4-yl-3,5-dihydro-4H-imidazol-4-one;
N-[3-(2-amino-1-methyl-5-oxo-4-pyridin-4-yl-4,5-dihydro-1H-imidazol-4-yl)phenyl]-2-methoxyacetamide;
N-[3-(2-amino-1-methyl-5-oxo-4-pyridin-4-yl-4,5-dihydro-1H-imidazol-4-yl)phenyl]-2-furamide;
3-(2-amino-1-methyl-5-oxo-4-pyridin-4-yl-4,5-dihydro-1H-imidazol-4-yl)-N-propylbenzamide;
2-amino-5-(3-bromophenyl)-3-methyl-5-(2-methylpyridin-4-yl)-3,5-dihydro-4H-imidazol-4-one;
2-amino-3-methyl-5-(2-methylpyridin-4-yl)-5-(3-pyridin-3-ylphenyl)-3,5-dihydro-4H-imidazol-4-one;
2-amino-3-methyl-5-(2-methylpyridin-4-yl)-5-(3-pyrimidin-5-ylphenyl)-3,5-dihydro-4H-imidazol-4-one;
2-amino-5-(2',5'-difluoro-1,1'-biphenyl-3-yl)-3-methyl-5-(2-methylpyridin-4-yl)-3,5-dihydro-4H-imidazol-4-one;
2-amino-5-(2-ethylpyridin-4-yl)-3-methyl-5-(3-pyridin-3-ylphenyl)-3,5-dihydro-4H-imidazol-4-one;
2-amino-5-(2-ethylpyridin-4-yl)-3-methyl-5-(3-pyrimidin-5-ylphenyl)-3,5-dihydro-4H-imidazol-4-one;
2-amino-5-(2',5'-difluoro-1,1'-biphenyl-3-yl)-5-(2-ethylpyridin-4-yl)-3-methyl-3,5-dihydro-4H-imidazol-4-one;
2-amino-3-methyl-5-(2-methylpyridin-4-yl)-5-(3-pyrazin-2-ylphenyl)-3,5-dihydro-4H-imidazol-4-one;
2-amino-5-(2-ethylpyridin-4-yl)-3-methyl-5-(3-pyrazin-2-ylphenyl)-3,5-dihydro-4H-imidazol-4-one;
2-amino-5-(2,6-dimethylpyridin-4-yl)-3-methyl-5-(3-pyridin-3-ylphenyl)-3,5-dihydro-4H-imidazol-4-one;
2-amino-5-(2,6-dimethylpyridin-4-yl)-3-methyl-5-(3-pyrimidin-5-ylphenyl)-3,5-dihydro-4H-imidazol-4-one;
2-amino-5-(2',5'-difluoro-1,1'-biphenyl-3-yl)-5-(2,6-dimethylpyridin-4-yl)-3-methyl-3,5-dihydro-4H-imidazol-4-one;
2-amino-5-(2,6-dimethylpyridin-4-yl)-3-methyl-5-(3-pyrazin-2-ylphenyl)-3,5-dihydro-4H-imidazol-4-one;
2-amino-5-(2,6-diethylpyridin-4-yl)-3-methyl-5-(3-pyridin-3-ylphenyl)-3,5-dihydro-4H-imidazol-4-one;
2-amino-3-methyl-5-pyridin-4-yl-5-(3-pyridin-3-ylphenyl)-3,5-dihydro-4H-imidazol-4-one;
a tautomer thereof;
a stereoisomer thereof; and
a pharmaceutically acceptable salt thereof.

* * * * *